United States Patent
Sulakvelidze et al.

(10) Patent No.: US 6,699,701 B1
(45) Date of Patent: *Mar. 2, 2004

(54) METHOD AND DEVICE FOR SANITATION USING BACTERIOPHAGES

(75) Inventors: Alexander Sulakvelidze, Baltimore, MD (US); J. Glenn Morris, Jr., Baltimore, MD (US); Zemphira Alavidze, Tbilisi (GE); Gary R. Pasternack, Baltimore, MD (US); Torrey C. Brown, Severna Park, MD (US)

(73) Assignee: Intralytix, Inc., Baltimore, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/757,687

(22) Filed: Jan. 11, 2001

Related U.S. Application Data

(60) Provisional application No. 60/205,240, filed on May 19, 2000, provisional application No. 60/175,415, filed on Jan. 11, 2000, provisional application No. 60/175,416, filed on Jan. 11, 2000, and provisional application No. 60/175,377, filed on Jan. 11, 2000.

(51) Int. Cl.[7] ................................. C12N 7/01
(52) U.S. Cl. .................... 435/235.1; 435/239; 435/263; 435/264; 435/267; 424/93.6; 424/404; 426/106; 426/129; 426/130; 426/133; 426/310; 426/323; 426/324; 426/532
(58) Field of Search ............................ 435/235.1, 239, 435/263, 264, 267; 426/326, 37, 42, 53, 61, 133, 310, 323, 324, 325, 532, 335, 106, 129, 130; 424/93.6, 404

(56) References Cited

U.S. PATENT DOCUMENTS

| | | |
|---|---|---|
| 2,876,108 A | 3/1959 | Taylor et al. |
| 4,375,734 A | 3/1983 | Kozloff et al. |
| 4,778,653 A | 10/1988 | Kamimura et al. |
| 4,851,240 A | 7/1989 | Day et al. |
| 4,891,210 A | 1/1990 | Norris |
| 4,957,686 A | 9/1990 | Norris |
| 5,006,347 A | 4/1991 | Day et al. |
| 5,132,221 A | 7/1992 | Ward et al. |
| 5,206,015 A | 4/1993 | Cox et al. |
| 5,573,801 A * | 11/1996 | Wilhoit .................... 426/326 |
| 5,576,035 A | 11/1996 | Bowling et al. |
| 5,612,182 A | 3/1997 | Pearson et al. |
| 5,641,464 A | 6/1997 | Briggs, III et al. |
| 5,660,812 A | 8/1997 | Merril et al. |
| 5,688,501 A | 11/1997 | Merril et al. |
| 5,766,892 A | 6/1998 | Merril et al. |
| 5,811,093 A | 9/1998 | Merril et al. |
| 5,869,113 A | 2/1999 | Clayton et al. |
| 6,039,984 A | 3/2000 | Bowling et al. |
| 6,121,036 A | 9/2000 | Ghanbari et al. |
| 6,322,783 B1 | 11/2001 | Takahashi |
| 6,461,608 B1 | 10/2002 | Averback et al. |
| 6,485,902 B2 | 11/2002 | Waddell et al. |

| | | |
|---|---|---|
| 2002/0001590 A1 | 1/2002 | Kelly et al. |

FOREIGN PATENT DOCUMENTS

| | | |
|---|---|---|
| DE | 37 14699 A1 | 1/1988 |
| DE | 43 26 617 C1 | 6/1994 |
| DE | 198 28 596 A1 | 2/1999 |
| EP | 0290295 | 11/1988 |
| EP | 0 290 295 A2 | 11/1988 |
| EP | 0 403 292 A2 | 12/1990 |
| EP | 0414304 | 2/1991 |
| EP | 0510907 | 10/1992 |
| EP | 0 970 613 A1 | 1/2000 |
| GB | 2253859 | 9/1992 |
| JP | 62123104 | 4/1987 |
| JP | 62298498 A | 12/1987 |
| JP | 1163108 A | 6/1989 |
| WO | WO9013631 | 11/1990 |
| WO | WO 90/14765 | 12/1990 |
| WO | 9527043 | 10/1995 |
| WO | WO 96/04364 | 2/1996 |
| WO | WO 97/13405 | 4/1997 |
| WO | 9739111 | 10/1997 |
| WO | WO 98/47521 | 10/1998 |
| WO | WO 98/54981 | 12/1998 |
| WO | WO 00/01799 | 1/2000 |
| WO | 0069269 | 11/2000 |

OTHER PUBLICATIONS

Greer et al. "Inability of a bacteriophage pool to control beef spoilage" *Interantional Journal of Food Microbiology*, vol. 10, Nos. 3–4 (May 1990), pp. 331–342.*

Barrow et al., "Use of Lytic Bacteriophage for Control of Experimental *Escherichia coli* Septicemia and Meningitis in Chickens and Calves," *Clin. Diagnostic Lab. Immun.*, vol. 5, No. 3, pp. 294–298 (May 1998).

Greer, "Homologous Bacteriophage Control of *Pseudomonas* Growth and Beef Spoilage," *J. Food Prot.*, vol. 49, No. 2, pp. 104–109 (Feb. 1986).

Kuhnen et al., "Establishment of a Typing System for Group D Streptococci," *Zentralblatt Fur Bakteriologie, Mikrobiologie, Und Hygiene, Series A, Medical Microbiology, Infectious Diseases, Virology, Parasitology*, vol. 267, No. 3, pp. 322–330 (Jan. 1988) (Abstract).

(List continued on next page.)

*Primary Examiner*—Jeffrey Stucker

(57) ABSTRACT

Methods and devices for sanitation using bacteriophage are disclosed. According to one embodiment of the present invention, a method for sanitation using at least one bacteriophage includes the steps of (1) storing the at least one bacteriophage in a container; and (2) applying the at least one bacteriophage to a surface to be sanitized with a dispersing mechanism. According to another embodiment of the present invention, a sanitation device that dispenses at least one bacteriophage includes a container, at least one bacteriophage stored in the container, and a dispersing mechanism that disperses the at least one bacteriophage from the container.

4 Claims, 1 Drawing Sheet

OTHER PUBLICATIONS

Leverentz et al., "Biocontrol of *Listeria Monocytogenes* on Fresh–Cut Produce by Treatment with Lytic Bacteriophages and a Bacteriocin," *Appl. Environ. Micro.*, vol. 69, No. 8, pp. 4519–4526 (Aug. 2003).

Leverentz et al., "Examination of Bacteriophage as a Biocontrol Method for *Salmonella* on Fresh–Cut Fruit: A Model Study," *J. Food Prot.*, vol. 64, No. 8, pp. 1116–1121 (Aug. 2001).

Tauxe, "Emerging Foodborne Diseases: An Evolving Public Health Challenge," *Emerging Infect. Diseases*, vol. 3, No. 4, pp. 425–434 (Oct.–Dec. 1997).

Whichard et al., "Suppression of *Salmonella* Growth by Wild–Type and Large–Plaque Variants of Bacteriophage Felix O1 in Liquid Culture and on Chicken Frankfurters," *J. Food Prot.*, vol. 66, No. 2, pp. 220–225 (Feb. 2003).

Alavidze, Z., et al., "Isolation of Specific Lytic Phases Against Multidrug Resistant *Pseudomonas aeruginosa,*" *American Society for Microbiology*, Final Program (1999).

Kudva, Indira T., et al., "Biocontrol of *Escherichia coli* O157 with O157–Specific Bacteriophages," *Applied and Environmental Microbiology*, 65:3767–3773 (1999).

Lenski, Richard E., "Dynamics of Interactions Between Bacteria and Virulent Bacteriphage," *Adv. Microb. Ecol.*, 10:1–44 (1988).

Levin, Bruce R., et al., "Phage Therapy Revisited: The Population Biology of a Bacterial Infection and its Treatment with Bacteriophage and Antibiotics," *The American Naturalist*, 147:881–898 (1996).

Ochs, Hans D., "Immunologic Responses to Bacteriophage φX 174 in Immunodeficiency Diseases," *Journal of Clinical Investigation*, 50:2559–2567 (1971).

Slopek et al., "Results of Bacteriophage Treatment of Suppurative Bacterial Infections; I. General Evaluation of the Results," *Arch. Immunol. Therapiae Exper.*, 31:267–291 (1983).

Slopek et al., "Results of Bacteriophage Treatment of Suppurative Bacterial Infections; II. Detailed Evaluation of the Results," *Arch. Immunol. Therapiae Exper.*, 31:293–327 (1981).

Slopek et al., "Results of Bacteriophage Treatment of Suppurative Bacterial Infections; III. Detailed Evaluation of the Results Obtained in Futher 150 Cases," *Arch. Immunol. Therapiae Exper.*, 32:317–335 (1984).

Slopek et al., "Results of Bacteriophage Treatment of Suppurative Bacterial Infections; IV. Evaluation of the Reults Obtained in 370 Cases," *Arch. Immunol. Therapiae Exper.*, 33:219–240 (1985).

Slopek et al., "Results of Bacteriophage Treatment of Suppurative Bacterial Infections; V. Evaluation of the Results Obtained I Children," *Arch. Immunol. Therapiae Exper.*, 33:241–260 (1985).

Slopek et al., "Results of Bacteriophage Treatment of Suppurative Bacterial Infections; VI. Analysis of Treatment of Suppurative Staphylococcal Infections," *Arch. Immunol. Therapiae Exper.*, 33:261–275 (1985).

Slopek et al., "Results of Bacteriophage Treatment of Suppurative Bacterial Infections in the Years 1981–1986," *Arch. Immunol. Therapiae Exper.*, 35:569–584 (1987).

Soothill, J.S., "Bacteriophage Prevents Destruction of Skin Grafts by *Pseudomonas aeruginosa,*" *Burns*, 20:209–211 (1994).

Soothill, J.S., "Treatment of Experimental Infections of Mice with Bacteriophages," *J. Med. Microbiol.*, 37:258–261 (1992).

Alavidze, A., et al., "Isolation of Specific Lytic Phages Against Multidrug Resistant Pseudomonas Aeruginosa," *The American Society for Microbiology*, 99:447 (1999). May 30–Jun. 3, 1999.

Slopek, S., et al., "Results of Bacteriophage Treatment of Suppurative Bacterial Infections VI. Analysis of Treatment of Suppurative Staphylococcal Infections," *Database Biosis 'Online, Biosciences Information Service*, (1985).

Bogovazova, G.G., et al., "Immunobiological Properties & Therapeutic Effectiveness of Preparations from Klebsiella Bacteriophages," *Zh. Mikrobiol. Epidemiol. Immunobiol.*, 3:30–33 (1992). Reviewed only the English Abstract.

Barrow, P.A., "Bacteriophages Mediating Somatic Antigenic Conversion in *Salmonella cholerae–suis*: their Isolation from Sewage and Other *Samonello* Serotypes Possessing the Somatic 6 Antigen," *Journal of General Microbiology*, 132:835–837 (1986).

Barrow, et al., "Salmonellosis—Prospects for Microbiological Control in Poultry," *Avian pathology*, 18:557–561 (1989).

Barrow, Paul A., et al., "Bacteriophage Therapy and Prophylaxis: Rediscovery and Renewed Assessment of Potential," *Trends in Microbiology*, 5:268–271 (1997).

Berchieri, A., Jr., et al., The Activity in the Chicken Alimentary Tract of Bacteriophages Lytic for *Salmonella Typhimurium, Res. Microbiol.*, 142:541–549 (1991).

Williams Smith, H., et al., "Successful Treatment of Experimental *Escherichia coli* Infections in Mice Using Phage: Its General Superiority Over Antibiotics," *Journal of General Microbiology*, 128:307–318 (1982).

Williams Smith, H., et al., "Effectiveness of Phages in Treating Experimental *Escherichia coli* Diarrhoea in Calves, Piglets and Lambs," *Journal of General Microbiology*, 129:2659–2675 (1983).

Williams Smith, H., et al., "The Control of Experimental *Escherichia coli* Diarrhoea in Calves by Means of Bacteriophages," *Journal of General Microbiology*, 133:1111–1126 (1987).

Soothill, J.S., et al., "The Efficacy of Phages in the Prevention of the Destruction of Pig Skin in vitro by *Pseudomonas aeruginosa*," Med. Sci. Res., 16:1287–1288 (1988).

Gachechiladze, K.K., et al., "Host–Controlled Modification and Restriction as a Criterion of Evaluating the Therapeutical Potential of *Pseudomonas* Phage," *J. Basic Microbiol.*, 31:101–106 (1991).

Adamia, Revaz S., et al., "The Virulent Bacteriophage IRA of *Samonella Typhimurium*: Cloning of Phage Genes Which are Potentially Lethal for the Host Cell," *J. Basic Microbiol.*, 30:707–716 (1990).

\* cited by examiner

METHOD AND DEVICE FOR SANITATION USING BACTERIOPHAGES

CROSS REFERENCE TO RELATED APPLICATIONS

The present application claims priority from U.S. Provisional Patent Application No. 60/175,416 filed Jan. 11, 2000, entitled "Method and Device for Sanitation Using a Bacteriophage" and U.S. Provisional Patent Application No. 60/205,240 filed May 19, 2000, entitled "Method and Device for Sanitation Using a Bacteriophage." The disclosures of these applications are incorporated, by reference, in their entireties.

In addition, the present application is related to the following U.S. Provisional Patent Applications: U.S. Provisional Patent Application No. 60/175,377 filed Jan. 11, 2000, entitled "Polymer Blends as Biodegradable Matrices for Preparing Biocomposites" and U.S. Provisional Patent Application No. 60/175,415 filed Jan. 11, 2000, entitled "Bacteriophage specific For Vancomycin Resistant Enterococci (VRE)." The disclosures of these applications are incorporated, by reference, in their entireties.

BACKGROUND OF THE INVENTION

1. Field of the Invention

The present invention is directed the field of bacteriophages. Specifically, it is directed to a method and device for sanitation using a bacteriophage.

2. Description of Related Art

Vancomycin-resistant Enterococcus

Over the last ten years there has been an emergence of bacterial pathogens, which demonstrate resistance to many, if not all antimicrobial agents. This is particularly relevant in the institutional environment where nosocomial pathogens are under selective pressure due to extensive antimicrobial usage. A particular problem in this regard has been vancomycin-resistant enterococci (VRE), which are not treatable with standard classes of antibiotics. Despite the recent release of two drugs to which VRE are susceptible (quinupristin/dalfopristin and linezolid [Plouffe JF, Emerging therapies for serious gram-positive bacterial infections: A focus on linezolid. Clin Infect dis 2000 Suppl 4:S144–9), these microorganisms remain an important cause of morbidity and mortality in immunocompromised patients.

Enterococci are gram positive facultatively anaerobic cocci found in a variety of environmental sources including soil, food and water. They are also a common colonizing bacterial species in the human intestinal tract (i.e., the intestinal tract serves as a reservoir for the microorganism). Although the taxonomy of enterococci has not been finalized, it is generally accepted that the genus consists of 19 species.

Antibiotic management of serious enterococcal infections has always been difficult due to the intrinsic resistance of the organisms to most antimicrobial agents [Arden, R. C, and B. E. Murray, 1994, "Enterococcus: Antimicrobial resistance." In: Principles and Practice of Infectious Diseases Update, volume 2, number 4 (February, 1994). New York: Churchill Livingstone, Inc. 15 pps; Landman, D., and J. M. Quale, 1997, "Management of infections due to resistant enterococci: a review of therapeutic options." *J. Antimicrob. Chemother.*, 40:161–70; Moellering, R. C., 1998, "Vancomcyin-resistant enterococci." *Clin. Infect. Dis.* 26:1196–9]. In the 1970's enterococcal infections were treated with the synergistic combination of a cell wall active agent such as penicillin and are aminoglycoside (Moellering, et al. (1971), "Synergy of penicillin and gentamicin against enterococci." *J Infect. Dis.*, 124:S207–9; Standiford, et al. (1970), "Antibiotic synergism of enterococci: relation to inhibitory concentrations." *Arch. Intern: Med.*, 126: 255–9). However, during the 1980's enterococcal strains with high levels of aminoglycoside resistance and resistance to penicillin, mediated both by a plasmid-encoded β-lactamase and by changes in penicillin binding proteins, appeared (Mederski-Samoraj, et al. (1983), "High level resistance to gentamicin in clinical isolates of enterococci." *J. Infect. Dis.*, 147:751–7; Uttley, et al. (1988), "Vancomycin resistant enterococci." *Lancet* i:57–8). In 1988 the first VRE isolates were identified (Leclercq, et al. (1988), "Plasmid mediated resistance to vancomycin and teicoplanin in *Enterococcus faecium.*" *N Engl. J: Med.*, 319:157–61). Such organisms, called VRE because of resistance to vancomycin, are also resistant to the penicillin-aminoglyroside combination. VRE includes strains of several different enterococcal species with clinically significant VRE infections caused by *Enterococcus faecium* and *Enterococcus faecalis.*

Enterococci can cause a variety of infections including wound infection, endocarditis, urinary tract infection and bacteremia. After *Staphylococcus aureus* and coagulase negative staphylococci, enterococci are the most common cause of nosocomial bacteremia. Among immunocompromised patients, intestinal colonization with VRE frequently precedes, and serves as a risk factor for, subsequent VRE bacteremia(Edmond, et al. (1995), "Vancomycin resistant *Enterococcus faecium* bacteremia: Risk factors for infection." *Clin. Inf. Dis.*, 20:1126–33; Tornieporth, N. G., R. B. Roberts, J. John, A. Hafner, and L. W. Riley, 1996, "Risk factors associated with vancomycin-resistant *Enterococcus faecium* infection or colonization in 145 matched case patients and control patients." *Clin. Infect. Dis.*, 23:767–72.]. By using pulse field gel electrophoresis as a molecular typing tool investigators at the University of Maryland at Baltimore and the Baltimore VA Medical Center have shown VRE strains causing bacteremia in cancer patients are almost always identical to those which colonize the patients gastrointestinal tract (Roghmann M C, Qaiyumi S, Johnson J A, Schwalbe R, Morris J G (1997), *"Recurrent vancomycin-resistant Enterococcus faecium bacteremia in a leukemia patient who was persistently colonized with vancomycin-resistant enterococci for two years."* Clin Infect Dis 24:514–5). The risk of acquiring VRE increases significantly when there is a high rate of VRE colonization among patients on a hospital ward or unit (i.e., when there is high "colonization pressure"). In one study in the Netherlands, colonization pressure was the most important variable affecting acquisition of VRE among patients in an intensive care unit (Bonten M J, et al, "The role of "colonization pressure" in the spread of vancomycin-resistant enterococci: an important infection control variable." Arch Intern Med 1998;25:1127–32). Use of antibiotics has been clearly shown to increase the density, or level of colonization, in an individual patient (Donskey C J et al, "Effects of antibiotic therapy on the density of vancomycin-resistant enterococci in the stool of colonized patients." N Engl J Med 2000;343:1925–32): this, in turn, would appear to increase the risk of subsequent infection, and the risk of transmission of the organism to other patients.

Multi-Drug Resistant *Staphylococcus aureus* (MDRSA)

*S. aureus* is responsible for a variety of diseases ranging from minor skin infections to life-threatening systemic infections, including endocarditis and sepsis [Lowy, F. D., 1998, "*Staphylococcus aureus* infections." *N. Engl. J. Med,*

8:520–532]. It is a common cause of community- and nosocomially-acquired septicemia (e.g., of approximately 2 million infections nosocomially acquired annually in the United States, approximately 260,000 are associated with *S. aureus* [Emori, T. G., and R. P. Gaynes, 1993, "An overview of nosocomial infections, including the role of the microbiology laboratory," *Clin. Microbiol. Rev.*, 4:428–442]). Also, approximately 20% of the human population is stably colonized with *S. aureus*, and up to 50% of the population is transiently colonized, with diabetics, intravenous drug users, patients on dialysis, and patients with AIDS having the highest rates of *S. aureus* colonization [Tenover, F. C., and R. P. Gaynes, 2000, "The epidemiology of Staphylococcus infections," p. 414–421, In: V. A. Fischetti, R. P. Novick, J. J. Ferretti, D. A. Portnoy, and J. I. Rood (ed), *Gram-positive pathogens*, American Society for Microbiology, Washington, D.C.]. The organism is responsible for approximately one-half of all skin and connective tissue infections, including folliculitis, cellulitis, furuncules, and pyomyositis, and is one of the most common causes of surgical site infections. The mortality rate for *S. aureus* septicemia ranges from 11 to 48% [Mortara, L. A., and A. S. Bayer, 1993, "Staphylococcus aureus bacteremia and endocarditis. New diagnostic and therapeutic concepts." *Infect. Dis. Clin. North. Am.*, 1:53–68].

Methicillin was one of the first synthetic antibiotics developed to treat penicillin-resistant staphylococcal infections. However, the prevalence of methicillin-resistant *S. aureus* strains or "MRSA" (which also are resistant to oxacillin and nafcillin) has drastically increased in the United States and abroad [Panlilio, A. L., D. H. Culver, R. P. Gaynes, S. Banerjee, T. S. Henderson, J. S. Tolson, and W. J. Martone, 1992, "Methicillin-resistant *Staphylococcus aureus* in U.S. hospitals, 1975–1991." *Infect. Control Hosp. Epidemiol.*, 10:582–586]. For example, according to the National Nosocomial Infections Surveillance System [National Nosocomial Infections Surveillance (NNIS) report, data summary from October 1986–April 1996, issued May 1996, "A report from the National Nosocomial Infections Surveillance (NNIS) System." *Am. J. Infect. Control.*, 5:380–388], approximately 29% of 50,574 *S. aureus* nosocomial infections from 1987 to 1997 were resistant to the β-lactam antibiotics (e.g., oxacillin, nafcillin, methicillin), and the percent of MRSA strains among U.S. hospitals reached approximately 40% by the end of the same period. At the University of Maryland Medical Center, >50% of all *S. aureus* blood isolates are now methicillin resistant.

In this setting, there is great concern about the possible emerge of methicillin-resistant/multi-drug resistant *S. aureus* strains which are vancomycin resistant—and which would be essentially untreatable. Although overt resistance to vancomycin has not yet been documented in clinical isolates, there have been several reports of clinical infections with *S. aureus* strains having intermediate resistance to vancomycin (MICs=8 μg/ml), which suggests that untreatable staphylococcal infections may not be too far away [Tenover, F. C., and R. P. Gaynes. 2000]. Given the virulence of *S. aureus*, the emergence of such untreatable strains would be devastating and have a major impact on the way in which medicine is practiced in this country.

Staphylococcal species, including MDRSA, are common colonizers of the human nose; in one community-based study, 35% of children and 28% of their guardians had nasal *Staphylococcus aureus* colonization (Shopsin B, et al, "Prevalence of methicillin-resistant and methicillin-susceptible *Staphylococcus aureus* in the community." J Infect Dis 2000;182:359–62.). Persons who are nasally colonized with MRSA have an increased risk of developing serious systemic infections with this microorganism, and, in particular, colonization or prior infection with MDRSA significantly increases the risk of subsequent bacteremia with MDRSA (Roghmann M C, "Predicting methicillin resistance and the effect of inadequate empiric therapy on survival in patients with *Staphylococcus aureus* bacteremia. Arch Intern Med 2000;160:1001–4). As seen with VRE, the rate of colonization of persons with MDRSA on a unit (the colonization pressure) significantly increases the risk of acquisition of MDRSA for other patients on the unit (Merrer J, et al, ""Colonization pressure" and risk of acquisition of methicillin-resistant *Staphylococcus aureus* in a medical intensive care unit." Infect Control Hosp Epidemiol 2000;21:718–23).

Multi-drug Resistant *Pseudomonas aeruginosa*

*Pseudomonas aeruginosa* is a highly virulent gram-negative bacterial species that is responsible for bacteremia, wound infections, pneumonia, and urinary tract infections. Increasing problems with multi-antibiotic resistance in Pseudomonas has been noted in hospitals, with particular concern focusing on strains which are generally designated as "Imipenem-resistant Pseudomonas", reflecting the last major antimicrobial agent to which they have become resistant. Many of these strains are resistant to all major antibiotic classes, presenting substantive difficulties in management of infected patients.

As seen with other Gram-negative microorganisms, Pseudomonas strains often emerge as the primary colonizing flora of the posterior pharynx during hospitalization. Strains present in the posterior pharynx, in turn, are more likely to be aspirated into the lungs, and cause pneumonia. In this setting, colonization with multi-drug resistant Pseudomonas represents a potentially serious risk factor for development of multi-drug resistant Pseudomonas pneumonia.

Bacteriophage

Bacteriophage has been used therapeutically for much of this century. Bacteriophage, which derive their name from the Greek word "phago" meaning "to eat" or "bacteria eaters", were independently discovered by Twort and independently by D'Herelle in the first part of the twentieth century. Early enthusiasm led to their use as both prophylaxis and therapy for diseases caused by bacteria. However the results from early studies to evaluate bacteriophage as antimicrobial agents were variable due to the uncontrolled study design and the inability to standardize reagents. Later in well designed and controlled studies it was concluded that bacteriophage were not useful as antimicrobial agents (Pyle, N. J. (1936), *J. Bacteriol.*, 12:245–61; Colvin, M. G. (1932), *J. Infect Dis.*, 51:17–29; Boyd et al. (1944), *Trans R. Soc. Trop. Med. Hyg.*, 37:243–62).

This initial failure of phage as antibacterial agents may have been due to the failure to select for phage that demonstrated high in vitro lytic activity prior to in vivo use. For example, the phage employed may have had little or no activity against the target pathogen, were used against bacteria that were resistant due to lysogenization or the phage itself might be lysogenic for the target bacterium (Barrow, et al. (1997), "Bacteriophage therapy and prophylaxis: rediscovery and renewed assessment of potential." *Trends in Microbiology*, 5:268–71). However, with a better understanding of the phage-bacterium interaction and of bacterial virulence factors, it was possible to conduct studies which demonstrated the in vivo anti-bacterial activity of the bacteriophage (Asheshov, et al. (1937), *Lancet*, 1:319–20; Ward, W. E. (1943), *J. Infect. Dis.*, 72:172–6; Lowbury, et al.

(1953), *J: Gen. Microbiol.,* 9:524–35). In the U.S. during the 1940's Eli Lilly commercially manufactured six phage products for human use including preparations targeted towards staphylococci, streptococci and other respiratory pathogens.

With the advent of antibiotics, the therapeutic use of phage gradually fell out of favor in the U.S. and Western Europe and little subsequent research was conducted. However, in the 1970's and 1980's there were reports of bacteriophage therapy continuing to be utilized in Eastern Europe, most notably in Poland and the former Soviet Union.

Phage therapy has been used in the former Soviet Union and Eastern Europe for over half a century, with research and production centered at the Eliava Institute of Bacteriophage in Tbilisi, in what is now the Republic of Georgia. The international literature contains several hundred reports on phage therapy, with the majority of the publications coming from researchers in the former Soviet Union and eastern European countries. To give but a few examples, phages have been reported to be effective in treating (i) skin and blood infections caused by Pseudomonas, Staphylococcus, Klebsiella, Proteus, and *E. coli* [Cislo, M., M. Dabrowski, B. Weber-Dabrowska, and A. Woyton, 1987, "Bacteriophage treatment of suppurative skin infections," 35(2):175–183; Slopek, S., I. Durlakowa, B. Weber-Dabrowska, A. Kucharewicz-Krukowska, M. Dabrowski, and R. Bisikiewicz, 1983, "Results of bacrteriophage treatment of suppurative bacterial infections. I. General evaluation of the results," *Archivum. Immunol. Therapiae Experimental,* 31:267–291; Slopek, S., B. Weber-Dabrowska, M. Dabrowski, and A. Kucharewicz-Krukowska, 1987, "Results of bacteriophage treatment of suppurative bacterial infections in the years 1981–1986,", 35:569–83], (ii) staphylococcal lung and pleural infections [Meladze, G. D., M. G. Mebuke, N. S. Chkhetia, N. I. Kiknadze, G. G. Koguashvili, I. I. Timoshuk, N. G. Larionova, and G. K. Vasadze, 1982, "The efficacy of Staphylococcal bacteriophage in treatment of purulent diseases of lungs and pleura," *Grudnaya Khirurgia,* 1:53–56 (in Russian, summary in English)], (iii) *P. aeruginosa* infections in cystic fibrosis patients [Shabalova, I. A., N. I. Karpanov, V. N. Krylov, T. O. Sharibjanova, and V. Z. Akhverdijan. "*Pseudomonas aeruginosa* bacteriophage in treatment of *P. aeruginosa* infection in cystic fibrosis patients," abstr. 443. In Proceedings of IX international cystic fibrosis congress, Dublin, Ireland], (iv) neonatal sepsis [Pavlenishvili, I., and T. Tsertsvadze. 1985. "Bacteriophage therapy and enterosorbtion in treatment of sepsis of newbornes caused by gram-negative bacteria." In abstracts, p. 104, Prenatal and Neonathal Infections, Toronto, Canada], and (v) surgical wound infections [Peremitina, L. D., E. A. Berillo, and A. G. Khvoles, 1981, "Experience in the therapeutic use of bacteriophage preparations in supportive surgical infections." *Zh. Mikrobiol. Epidemiol. Immunobiol.* 9:109–110 (in Russian)]. Several reviews of the therapeutic use of phages were published during the 1930s–40s [Eaton, M. D., and S. Bayne-Jones, 1934, "Bacteriophage therapy: review of the principles and results of the use of bacteriophage in the treatment of infections," *J. Am. Med. Assoc.,* p. 103; Krueger, A. P., and E. J. Scribner, 1941, "The bacteriophage: its nature and its therapeutic use," *J. Am. Med. Assoc.,* p. 116] and recently [Barrow, P. A., and J. S. Soothill, 1997, "Bacteriophage therapy and propylaxis—rediscovery and renewed assessment of potential," *Trends in Microbiol.,* 5(7):268–271; Lederberg, J., 1996, "Smaller fleas . . . ad infinitum: therapeutic bacteriophage," *Proc. Natl. Acad. Sci. USA,* 93:3167–3168]. In a recent paper published in the Journal of Infection (Alisky, J., K. Iczkowski, A. Rapoport, and N. Troitsky, 1998, "Bacteriophages show promise as antimicrobial agents," *J. Infect.,* 36:5–15), the authors reviewed Medline citations (published during 1966–1996) of the therapeutic use of phages in humans. There were twenty-seven papers from Britain, the U.S.A., Poland and the Soviet Union, and they found that the overall reported success rate for phage therapy was in the range of 80–95%.

These are several British studies describing controlled trials of bacteriophage raised against specific pathogens in experimentally infected animal models such as mice and guinea pigs (See, e.g., Smith. H. W., and M. B. Huggins "Successful treatment of experimental *Escherichia coli* infections in mice using phages: its general superiority over antibiotics" *J. Gen. Microbial.,* 128:307–318 (1982); Smith, H. W., and M. B. Huggins "Effectiveness of phages in treating experimental *E. coli* diarrhea in calves, piglets and lambs" *J. Gen. Microbiol.,* 129:2659–2675 (1983); Smith, H. W. and R. B. Huggins "The control of experimental *E. coli* diarrhea in calves by means of bacteriophage". *J. Gen. Microbial.,* 133:1111–1126 (1987); Smith, H. W., R. B. Huggins and K. M. Shaw "Factors influencing the survival and multiplication of bacteriophages in calves and in their environment" *J. Gen. Microbial.,* 133:1127–1135 (1987)). These trials measured objective criteria such as survival rates. Efficacy against Staphylococcus, Pseudomonas and Acinetobacter infections were observed. These studies are described in more detail below.

One U.S. study concentrated on improving bioavailability of phage in live animals (Merril, C. R., B. Biswas, R. Carlton, N. C. Jensen, G. J. Greed, S. Zullo, S. Adhya "Long-circulating bacteriophage as antibacterial agents" *Proc. Natl. Acad Sci. USA,* 93:3188–3192 (1996)). Reports from the U.S. relating to bacteriophage administration for diagnostic purposes have indicated phage have been safely administered to humans in order to monitor humoral immune response in adenosine deaminase deficient patients (Ochs, et al. (1992), "Antibody responses to bacteriophage phi X174 in patients with adenosine deaminase deficiency." *Blood,* 80:1163–71) and for analyzing the importance of cell associated molecules in modulating the immune response in humans (Ochs, et al. (1993), "Regulation of antibody responses: the role of complement acrd adhesion molecules." *Clin. Immunol. Immunopathol.,* 67:S33–40).

Additionally, Polish, Georgian, and Russian papers describe experiments where phage was administered systemically, topically or orally to treat a wide variety of antimicrobial resistant pathogens (See, e.g., Shabalova, I. A., N. I. Karpanov, V. N. Krylov, T. O. Sharibjanova, and V. Z. Akhverdijan. "*Pseudomonas aeruginosa* bacteriophage in treatment of *P. aeruginosa* infection in cystic fibrosis patients," Abstr. 443. In Proceedings of IX International Cystic Fibrosis Congress, Dublin, Ireland; Slopek, S., I. Durlakowa, B. Weber-Dabrowska, A. Kucharewicz-Krukowska, M. Dabrowski, and R Bisikiewicz. 1983. "Results of bacteriophage treatment of suppurative bacterial infections. I. General evaluation of the results." *Archivum, Immunol. Therapiae Experimental,* 31:267–291; Slopek, S., B. Weber-Dabrowska, M. Dabrowski, and A. Kucharewicz-Krukowska. 1987. "Results of bacteriophage treatment of suppurative bacterial infections in the years 1981–1986", *Archivum Immunol. Therapiae Experimental,* 35:569–83.

Infections treated with bacteriophage included osteomyelitis, sepsis, empyema, gastroenteritis, suppurative wound infection, pneumonia and dermatitis. Pathogens involved included Staphylococci, Sreptococci, Klebsiella, Shigella, Salmonella, Pseudomonas, Proteus and Escherichia. These articles reported a range of success rates for phage therapy between 80–95% with only rare reversible allergic or gastrointestinal side effects. These results indicate that bacteriophage may be a useful adjunct in the fight against bacterial diseases. However, this literature does not describe, in any way anticipate, or otherwise suggest the use of bacteriophage to modify the composition of colonizing bacterial flora in humans, thereby reducing the risk of subsequent development of active infections.

Salmonella in Humans

Salmonella are the leading cause of food-borne disease in the United States. In 1993, USDA estimated that there were between 700,000 and 3.8 million Salmonella cases in this country, with associated medical costs and productivity losses of between $600 million and $3.5 billion. See Food Safety and Inspection Service, 1995; 9 CFR Part 308; Pathogen Reduction; Hazard Analysis and Critical Control Point (HACCP) Systems; Proposed Rule 60 Fed. Reg. 6774–6889; FoodNet, unpublished data. More exact estimates of incidence have come from CDC's FoodNet system, based on active surveillance data from seven sentinel sites, with the most recent data suggesting that there are 1.4 million cases annually. See Mead, P. S., L. Slutsker, V. Dietz, L. F. McCaig, J. S. Bresee, C. Shapiro, P. M. Griffin, and R. V. Tauxe "Food-related illness and death in the United States" *Emerg. Infec. Dis.* 5:607–625 (1999). While all Salmonella appear to be able to cause illness, *S. typhimurium* and *S. enteritidis* accounted for 22.6% and 22% of all human cases, respectively, in the United States between 1991 and 1995. See Centers for Disease Control and Prevention "Salmonella Surveillance, Annual Summary" 1991, 1992, 1993–1995.

*S. typhimurium* has become of particular concern because of the recent emergence of a highly antibiotic resistant strain (resistant to ampicillin, chloramphenicol, streptomycin, sulfonamides, and tetracycline) designated as definitive type 104 (DT104). In 1979–80, this resistance pattern was seen in 0.6% of *S. typhimurium* isolates; by 1996, 34% of all U.S. isolates tested by public health laboratories had this pattern, with further testing showing that approximately 90% of these resistant isolates were DT104. See Glynn, M. K., C. Bopp, W. DeWitt, P. Dabney, M. Mokhtar, and F. J. Angulo "Emergence of multidrug-resistant *Salmonella enterica* serotype typhimurium DT104 infections in the United States" *N. Eng. J. Med.* 19:1333–8 (1988). Recent data also suggest that DT-104 is beginning to acquire resistance to trimethoprim and quinolones. See Wall, P. G., D. Morgan, K. Lamden. M. Ryan, M. Griffin, E. J. Threlfall, L. R. Ward, and B. Rowe "A case control study of infection with an epidemic strain of multiresistant *Salmonella typhimurium* DT104 in England and Wales" *Commun. Dis. Rep.* CDR Rev. 4:R130–8135 (1994). While data on pathogenicity are limited, DT104 appears to be responsible for increased human morbidity and mortality, as compared with other Salmonella. See Centers for Disease Control "Multidrug resistant Salmonella serotype typhimurium—United States, 1996" *Morbid Mortal Weekly Rep.* 46:308–10 (1997).

Among *S. enteritidis* isolates, attention has focused on phage types 8 and 4. Phage type 8 accounts for approximately half of all U.S. *S. enteritidis* isolates. See Hickman-Brenner, F. W., A. D. Stubbs, and J. J. Farmer, III "Phage typing of *Salmonella enteritidis* in the United States" J. Clin. Microbiol., 29;2817–23 (1991); Morris, J. G., Jr., D. M. Dwyer, C. W. Hoge, A. D. Stubbs, D. Tilghman, C. Groves, E. Israel, and J. P. Libonati "Changing clonal patterns of *Salmonella enteritidis* in Maryland: An evaluation of strains isolated between 1985–90" *J. Clin. Microbiol.*, 30:1301–1303 (1992). Phage type 4 is seen less frequently, but has been associated with recent major outbreaks; it clearly has increased virulence in chickens, and, again, may have increased virulence in humans. See Humphrey T. J., Williams A., McAlpine K., Lever M. S., Guard-Petter J., and J. M. Cox "Isolates of *Salmonella enterica* Enteritidis PT4 with enhanced heat and acid tolerance are more virulent in mice and more invasive in chickens" *Epidemiol. Infect.* 117:79–88 (1996); Rampling, A., J. R. Anderson, R. Upson, E. Peters, L. R. Ward, and B. Rowe "*Salmonella enteritidis* phage type 4 infection of broiler chickens: a hazard to public health" *Lancet*, ii:436–8 (1989).

In healthy adults, Salmonella generally causes a self-limited diarrheal illness; however, these individuals may asymptomatically carry the organism in their intestinal tract for six months or more after cessation of symptoms (convalescent carriage), serving as one source for continue transmission of the organism in the community. The elderly, the very young, and persons who are immunocompromised are at risk for Salmonella bacteremia, which may occur in as many as 5% of infected "high risk" patients. See Taylor, J. L., D. M. Dwyer, C. Groves, A. Bailowitz, D. Tilghman, V. Kim, A. Joseph, and J. G. Morris, Jr. "Simultaneous outbreak of *Salmonella enteritidis* and *Salmonella schwarzengrund* in a nursing home: association of *S. enteritidis* with bacteremia and hospitalization" *J. Infect. Dis.* 167:781–2 (1993). Between 1% and 3% of infected persons may also develop reactive arthritis, with the possibility of associated long-term disability.

Antibiotic therapy of diarrheal illness is not effective, and may actually prolong intestinal carriage. See Alavidze, Z., and I. Okolov "Use of specific bacteriophages in prophylaxis of intrahospital infections caused by P. aeruginosa" In: *Abst., All-Soviet Union conference* "Modern biology at the service of public health," Kiev, Ukraine (1988). Bacteremia is, obviously, treated with antibiotics, although the emergence of highly resistant strains such as DT104 has begun to create problems in patient management. See Wail, P. G., D. Morgan, K. Lamden, M. Ryan, M. Griffin, E. J. Threlfall, L. R. Ward, and B. Rowe "A case control study of infection with an epidemic strain of multiresistant *Salmonella typhimurium* DT104 in England and Wales" *Commun. Dis. Rep.* CDR Rev. 4-R130–RI35 (1994). There is currently no effective means of limiting or eradicating carriage of the organism in the intestinal tract. See Neill, M. A., S. M. Opal, J. Heelan, R. Giusti, J. E. Cassidy, R. White, and K. H. Mayer "Failure of ciprofloxacin to eradicate convalescent fecal excretion after acute Salmonellosis: experience during an outbreak in health care workers" *Ann. Intern Med.* 119:195–9 (1991).

Salmonella in Chickens

USDA estimates that in 50–75% of human Salmonella cases the microorganism is acquired from meat, poultry, or eggs, with poultry serving as the primary vehicle of transmission. Salmonella are part of the normal, colonizing intestinal flora in many animals, including chickens. Studies conducted in the early 1990's by USDA indicated that 20–25% of broiler carcasses and 18% of turkey carcasses were contaminated with Salmonella prior to sale. See Food Safety and Inspection Service (1995); 9 CFR Part 308; Pathogen Reduction; Hazard Analysis and Critical Control Point (HACCP) Systems; Proposed Rule; 60 Fed. Reg. 6774–6889.

Contamination may result from rupture of the intestinal tract during slaughter. However, with current slaughter techniques, removal of the viscera seldom results in intestinal rupture and carcass contamination—and, when it does occur, the carcass is immediately tagged for "reprocessing." The more common source of Salmonella is the skin of the animal itself, with the feather follicles serving as a sanctuary for bacteria. In contrast to beef, chickens are slaughtered "skin on," so that antemortem contamination of feathers becomes an important element in determining whether Salmonella can be isolated from the carcass. The close quarters in chicken houses, and the piling of chicken crates on trucks on the way to slaughterhouses, results in frequent contamination of feathers by feces. If members of a flock have high levels of intestinal colonization with Salmonella, there are multiple opportunities for contamination of feathers and feather follicles with the microorganism, and, in turn, for Salmonella contamination of the final product.

According to the CDC FoodNet/Salmonella surveillance system, the five most common human Salmonella isolates in the United States during 1990–1995 were S. typhimurium, S. enteritidis, S. heidelberg, S. newport, and S. hadar. Further, according to the USDA/FSIS data, the five most common Salmonella serotypes isolated from broiler chickens during the same period were S. heidelberg, S. kentucki, S. hadar, S. typhimurium, and S. thomson. While Applicants do not consider this to be an exhaustive list, Applicants note that these are common Salmonella isolates and serotypes.

The rate of Salmonella contamination of poultry carcasses was a major focus of the recently implemented revision of the national food safety regulations (Pathogen Reduction; Hazard Analysis and Critical Control Point (HACCP) Systems), which mandates government testing for Salmonella in all slaughter plants. Regulations now in effect require that product be tested by putting a whole chicken carcass in a "baggie" with culture media and shaking; growth of any Salmonella from broth counts as a positive test. Plants must meet specific standards for percentage of product contaminated, based on national averages; failure to meet these standards results in plant closure. See Food Safety Inspection Service (1996); 9 CFR Part 304, et seq.; Pathogen Reduction; Hazard Analysis and Critical Control Point (HACCP) Systems; Final Rule 61 Fed. Reg. 38806–989. Concerns about Salmonella contamination have also become a major issue in international trade, with Russia and other countries having embargoed millions of dollars worth lots of chickens because of identification of Salmonella in the product.

In this environment, there are strong public health, regulatory, and trade incentives for producers to reduce levels of Salmonella contamination in poultry. Irradiation of raw product (i.e., chicken carcasses) is efficacious, but expensive, and is limited by the small number of irradiation facilities and by consumer acceptance. Treatment of chickens with antibiotics does not eradicate colonization, tending simply to select out for more resistant organisms. Antibiotics (in contrast to phage) generally have activity against multiple bacterial species; their administration can result in serious perturbations in the microbial ecology of the animal's intestinal tract, with accompanying loss of "colonization resistance" and overgrowth of microorganisms that are resistant to the antimicrobial agent used. Vaccination is similarly ineffective in elimination of Salmonella. See Hassan, J. O., and R. Curtiss, III "Efficacy of a live avriulent Salmonella typhimurium vaccine in preventing colonization and invasion of laying hens by Salmonella typhimurium and Salmonella enteritidis" Avian. Dis. 41:783–91 (1997); Methner, U., P. A. Barrow, G. Martin, and H. Meyer "Comparative study of the protective effect against Salmonella colonization in newly hatched SPF chickens using live, attenuated Salmonella vaccine strains, wild-type Salmonella strains or a competitive exclusion product" Int. J Food Microbiol., 35:223–230 (1997); Tan, S., C. L. Gyles, and B. N. Wilkie "Evaluation of an aroA mutant Salmonella typhimurium vaccine in chickens using modified semisolid Rappaport Vassiliadis medium to monitor fecal shedding" Vet. Microbiol., 54:247–54 (1997).

Competitive exclusion (i.e., administration of "good" bacteria to "crowd out" Salmonella and other "bad" bacteria) has shown variable success. See Palmu, L, I. Camelin "The use of competative exclusion in broilers to reduce the level of Salmonella contamination on the farm and at the processing plant" Poultry Sci. 76:1501–5 (1997). There is now a commercially available competitive exclusion product, PreEmpt (produced by MS Bioscience), that consists of 27 different bacteria strains- In preliminary testing, it appears to be effective in limiting Salmonella colonization, but its usage is hampered by the cost. Most importantly, its efficacy is significantly decreased if antibiotics are administered to animals as growth additives (a standard practice in the poultry industry).

In the absence of any other definitive means of eradicating the organism, USDA has articulated the concept of Salmonella control through a "multiple hurdle" approach, encouraging implementation of procedures to reduce the risk of contamination during slaughter while at the same time seeking to limit colonization/contamination of broiler flocks by the organism. Under these circumstances, there is a clear market for products and approaches that can be used as part of an overall program of Salmonella control. Any such product should be cheap, safe, and easy to use-, there would also be potential advantages for products which could be targeted toward specific pathogens, such as S. enteritidis PT4 and S. typhimurium DT104.

SUMMARY OF THE INVENTION

According to one embodiment of the present invention, a method for sanitation using at least one bacteriophage is disclosed. The method includes the steps of (1) storing the at least one bacteriophage in a container; and (2) applying the at least one bacteriophage to a surface to be sanitized with a dispersing mechanism.

The container may be, inter alia, a pressurized container (e.g., a aerosol canister), may be a fogging device; may be a trigger spray device; or may be a pump spray device. The bacteriophage may be poured, brushed, wiped, painted, or coated on the area or an object. The bacteriophage may be transferred from a transfer vehicle, which may be a towel, a sponge, a roller, a paper product, a towelette, etc., to the area or object. In one embodiment, hoses or sprinklers may be used. Once applied, the area or object may be flushed with water.

The areas or objects that may have the bacteriophage applied include, inter alia, livestock pens, live stock feeding areas, live stock slaughter areas, live stock waste areas, knives, shovels, rakes, saws, livestock handling devices, hospital rooms, operating rooms, bathrooms, waiting rooms, beds, chairs, wheel chairs, gurneys, surgical tables, operating room floors, operating room walls, surfaces in an intensive care unit, electrocardiographs, respirators, cardiovascular assist devices, intraaortic balloon pumps, infusion devices, other patient care devices, televisions, monitors, remote controls, and telephones. The present invention may be used to decontaminate military equipment, including aircraft, vehicles, electronic equipment, and weapons.

According to another embodiment of the present invention, a sanitation device that dispenses at least one bacteriophage is disclosed. The device includes a container, at least one bacteriophage stored in the container, and a dispersing mechanism that disperses the at least one bacteriophage from the container.

According to another embodiment of the present invention, a method for poultry processing sanitation with at least one bacteriophage is disclosed. The method includes the step of applying at least one bacteriophage to fertilized eggs.

According to another embodiment of the present invention, a method for poultry processing sanitation with at least one bacteriophage is disclosed. The method includes the step of applying at least bacteriophage to at least one freshly-hatched bird.

According to another embodiment of the present invention, a method for poultry processing sanitation with at least one bacteriophage is disclosed. The method includes the step of providing drinking water containing at least bacteriophage.

According to another embodiment of the present invention, a method for poultry processing sanitation with at least one bacteriophage is disclosed. The method includes the step of providing food with the at least bacteriophage.

According to another embodiment of the present invention, a method for poultry processing sanitation with at least one bacteriophage is disclosed. The method includes the step of applying at least one bacteriophage to post-chill birds.

Developing novel methodologies/antimicrobials for reducing poultry contamination with Salmonella may be expected to have tremendous impact on human health; these antimicrobials also may have utility in managing infections caused by multi drug-resistant Salmonella (e.g., DT104) strains. It is an object of this invention to isolate and characterize phages that may have utility in managing Salmonella infections. The present inventors have isolated several bacteriophages active against genetically diverse Salmonella strains, and have demonstrated the utility of these phages in cleaning Salmonella contaminated surfaces. These phages may be used in managing Salmonella-contamination and prophylaxis/treatment of diseases caused by Salmonella, including multidrug resistant DT-104 strains.

One attractive modality to control the rates of Salmonella contamination of poultry is to use Salmonella-specific bacteriophages. Bacteriophages are specific for prokaryotes, and they are highly selective for a bacterial species or serotype (i.e., they permit targeting of specific bacteria, without disrupting normal flora). In addition, phages are relatively, easy to propagate and purify on a production scale. Furthermore, extensive studies in the Soviet Union and several Eastern European countries have demonstrated the safety and efficacy of bacteriophage therapy for many bacterial diseases. Extending the concept of phage treatment to the primary prevention of salmonellosis, by (i) administering specific phages to chickens, and (ii) using phages for environmental clean-up of chicken houses, processing plants, etc., may reduce or eliminate Salmonella strains which ate of ma or public health significance.

According to another embodiment of the present invention, a method for foodstuff packaging is disclosed. The method includes the steps of (1) providing foodstuff for packaging: (2) applying at least one bacteriophage to the foodstuff; and (3) packaging the foodstuff with a packaging material.

According to another embodiment of the present invention, a method for foodstuff packaging is disclosed. The method includes the steps of (1) providing a package containing the foodstuff; and (2) inserting a matrix containing at least one bacteriophage into the package.

According to another embodiment of the present invention, a method for foodstuff packaging is disclosed. The method includes the steps of (1) providing a foodstuff; (2) providing a packaging material comprising at least one bacteriophage; and (3) packaging the foodstuff with the packaging material.

According to another embodiment of the present invention, a method for foodstuff sanitation with at least one bacteriophage is disclosed. The method includes the steps of (1) providing a foodstuff; and (2) applying the at least one bacteriophage to the foodstuff.

According to another embodiment of the present invention, a method for decontamination using at least one bacteriophage is disclosed. The method includes the step of applying at least one bacteriophage to an area contaminated with at least one pathogenic bacteria.

DETAILED DESCRIPTION OF THE EMBODIMENTS

Figure 1:
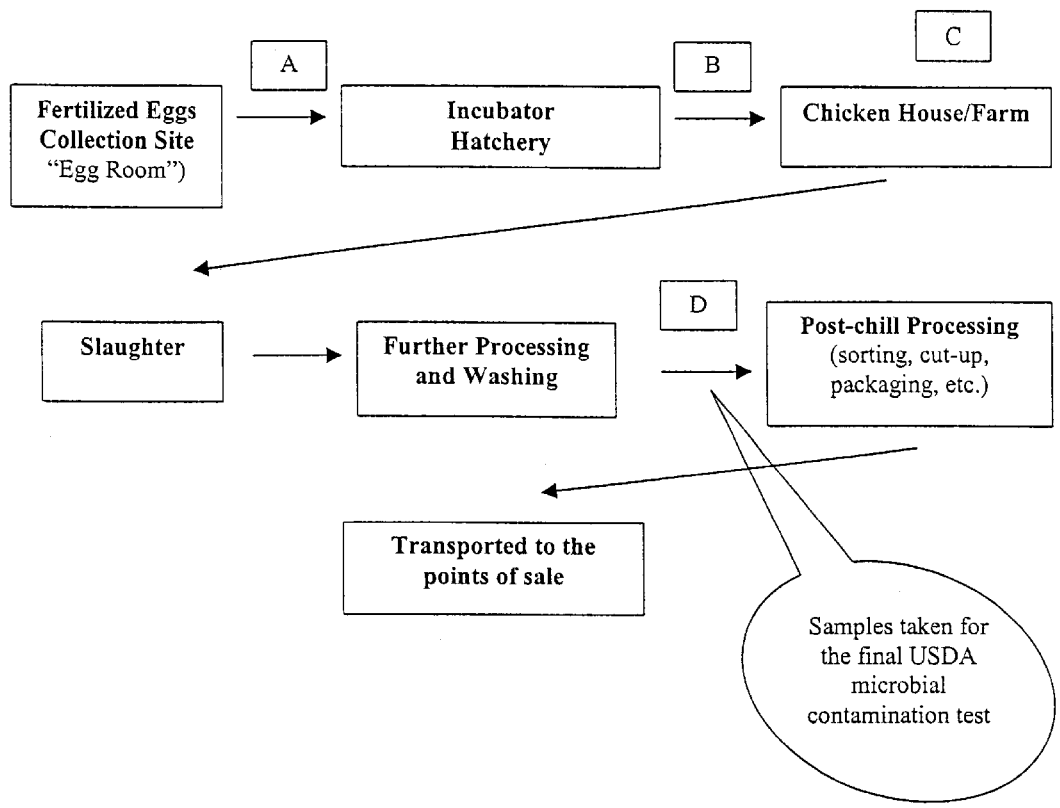
FIG. 1 is a schematic of a poultry processing scheme according to one embodiment of the present invention.

Bacteriophage technology can be of value in managing a large variety of bacterial infections because: (i) bacteriophages are highly specific and very effective in lysing targeted pathogenic bacteria, (ii) bacteriophages are absolutely specific for prokaryotes, and do not affect humans or animals, (iii) bacteriophages are safe, as underscored by their extensive clinical use in Eastern Europe and the former Soviet Union, and the commercial sale of phages in the 1940's in the United States, (iv) phage preparations can rapidly be modified to combat the emergence of newly arising bacterial threats, and (v) phage production is seen to be cost-effective for large-scale applications in a variety of medical settings. Of particular relevance, bacteriophage will not kill non-pathogenic, "normal flora" bacteria, thereby retaining the "colonization resistance" of reservoirs such as the human intestinal tract, the nose, and the posterior pharynx. Accordingly, the present invention envisions using lytic phages (in combination with antibiotics or alone) to prophylactically or therapeutically eliminate various bacteria capable of causing diseases of the gastrointestinal, genitourinary, and respiratory tracts, and skin, oral cavity, and bloodstream. In accordance with this invention, therapeutic phages can be administered in a number of ways, in various formulations, including: (i) orally, in tablets or liquids, (ii) locally, in tampons, rinses or creams, (iii) aerosols, and (iv) intravenously.

One benefit of bacteriophage therapy when compared to antibiotic therapy relates to the relative specificity of the two therapeutic modalities. Bacteriophage are specific for particular bacterial strains or species, while antibiotics typically are broadly effective against a large multiplicity of bacterial species or genera. It is well known that normal individuals are colonized with innocuous bacteria, and this colonization may be beneficial to the colonized individual (see U.S. Pat. No. 6,132,710, incorporated herein by reference). Antibiotic therapy can severely alter colonization or even eliminate beneficial colonization completely. This often has have adverse effects, such as the outgrowth of opportunistic species such as *Clostridium difficile,* which then leads to an antibiotic-associated colitis. Similarly, antibiotic therapy with its well-known adverse effect upon colonization with normal flora leads to increased density of VRE colonization (see Donskey V. J. et al., Effect of Antibiotic Therapy on the Density of Vancomycin-Resistant Enterococci in the Stool of Colonized Patients. *New England Journal f Medicine,* 2000, 343:1925–1932.) In contrast, bacteriophage therapy specifically affects the bacterial strains that are sensitive or susceptible to lytic infection by the particular bacteriophage in the therapeutic composition, but leaves other (innocuous or beneficial) bacteria unaffected. Thus, bacteriophage therapy is preferable for prophylactic treatment where alteration of normal microflora should be minimized.

In a preferred mode of this invention, phage technology is focused on two important human pathogens, VRE and MDRSA, and the value of VRE- and MDRSA-specific lytic phages in different settings: (i) oral administration of phages for prophylaxis against septicemia, (ii) local application of phages for prophylaxis/treatment of skin and wound infections, (iii) intravenous administration of phages for therapy of septicemia, and (iv) the use of aerosolized phages against respiratory pathogens.

VRE infection has become a particularly serious problem among immunocompromised and/or seriously ill patients in intensive care units, cancer centers and organ transplant units. Since VRE are resistant to all currently used antimicrobials, alternate approaches to reducing or eliminating VRE gastrointestinal colonization in immunocompromised patients must be found in order to reduce the prevalence of VRE bacteremia. Oral administration of lytic bacteriophage active against VRE is one such approach.

The general rule is that patients first become colonized by pathogenic bacteria present in their immediate environment before developing illness due to those bacteria. Serious VRE infections, including septicemia, usually are preceded by intestinal colonization with the infecting organisms; therefore, the risk of septicemia is likely to be decreased by reducing colonization prior to periods when patients are severely neutropenic or otherwise immunosuppressed (i.e., reducing intestinal colonization may also reduce the risk of bloodstream invasion). The present inventors have discovered that certain strains of bacteriophage are particularly effective at lysing VRE. By administering these VRE-active bacteriophage to persons colonized with VRE, it is possible to substantially reduce or even eliminate VRE from the colonized person. Thus, the present invention provides strains of phage which are particularly effective against VRE, methods for obtaining additional strains of VRE-active phage, methods for treating patients colonized with VRE by administering VRE-active phage, and methods of reducing nosicomial infection rate by administering VRE-active phage in vivo, ex vivo, or both, to selected locations, areas, objects and/or persons.

Analogous approaches using bacteriophage targeted to other pathogenic bacteria are also contemplated by this invention. *S. aureus* phage preparations can reduce contamination of skin and wounds with *S. aureus,* which in turn may prevent the development of serious surgical site infections and septicemia. Phage active against Pseudomonas species can be used to reduce colonization that threatens to develop into pneumonia in immunocompromised patients or in individuals suffering from cystic fibrosis.

VRE-active Bacteriophage

The present inventors have isolated several lytic phages active against genetically diverse (as assessed by pulsed field gel electrophoresis and/or arbitrary pruned polymerase chain reaction or other nucleic acid amplification techniques) VRE strains. In vitro susceptibility tests involving 234 VRE strains (184 *E. faecium,* 41 *E. faecalis* and 6 *E. gallinarium* isolated from patients at the University of Maryland and the Baltimore VA Medical Center, and 3 *E. faecium* ATCC strains), resulted in the Intralytix phage collection being able to cumulatively lyse all VRE strains in the collection, with one particular phage being able to lyse 95% of VRE strains. Furthermore mice whose gastrointestinal tract was colonized with VRE under selective pressure of antibiotic administration, were orogastrically administered VRE-active phages, which resulted in a 1 to 3 log reduction of VRE gastrointestinal colonization compared to a control group of animals not given phage. This occurred within a 48 to 72 hour time frame. No side effects due to the phage were observed.

Bacteriophage strains may be isolated by analogous procedures to those used to isolate the VRE-active strains described herein. Suitable bacteriophage may be isolated from any sample containing bacteriophage, which typically are found in association with their host bacteria. Thus, any source that might be expected to contain VRE is suitable for use as a source of VRE-active bacteriophage. Such samples include fecal, urine, or sputum samples from patients, particularly patients undergoing acute or prophylactic antibiotic therapy, patients in intensive care units or immunocompromised patients. Such patients may include but are not limited to burn patients, trauma patients, patients receiving bone marrow and/or organ transplants, cancer patients, patients with congenital or acquired immunodeficiency diseases, dialysis patients, liver disease patients, and patients with acute or chronic renal failure. Body fluids including ascites, pleural effusions, joint effusions, abscess fluids, and material obtained from wounds. While humans are the primary reservoir for VRE, the organism also can be readily found in the immediate environment of infected/colonized patients such as bedrails, bed sheets, furniture, etc. (Bodnar, U. R. et al (1996), "Use of in house studies of molecular epidemiology and full species identification of controlling spread of vancomycin resistant Enterococcus faecalis isolates", *J. Clin. Microbiol.,* 34: 2129–32; Bonten, M. J. M. et al (1996), "Epidemiology of colonization of patients and the environment with vancomycin resistant enterococci." *Lancet,* 348: 1615–19; Noskin, G. A. (1995), "Recovery of vancomycin resistant enterococci on fingertips and environmental surfaces." *Infect. Control Hosp. Epidemiol.,* 16: 577–81). Consequently, samples for bacteriophage isolation may also be obtained from nonpatient sources, including sewage, especially sewage streams near intensive care units or other hospital venues, or by swab in hospital areas associated with risk of nosicomial infection, such as intensive care units. Other suitable sampling sites include nursing homes, rest homes, military barracks, dormitories, classrooms, and medical waste facilities. Phages also can be isolated from rivers and lakes, wells, water tables, as well as other water sources (including salt water). Preferred sampling sites include water sources near likely sites of contamination listed above.

Suitable methods for isolating pure bacteriophage strains from a bacteriophage-containing sample are well known, and such methods may be adapted by the skilled artisan in view of the guidance provided herein. Isolation of VRE-active bacteriophage from suitable samples typically proceeds by mixing the sample with nutrient broth, inoculating the broth with a host bacterial strain, and incubating to enrich the mixture with bacteriophage that can infect the host strain. An Enterococcus sp. strain will be used as the host strain, preferably a VRE strain. After the incubation for enrichment, the mixture is filtered to remove bacterial leaving lytic bacteriophage in the filtrate. Serial dilutions of the filtrate are plated on a lawn of VRE, and VRE-active phage infect and lyse neighboring bacteria. However the agar limits the physical spread of the phage throughout the plate, resulting in small visibly clear areas called plaques on the plate where bacteriophage has destroyed VRE within the confluent lawn of VRE growth. Since one plaque with a distinct morphology represents one phage particle that replicated in VRE within that area of the bacterial lawn, the purity of a bacteriophage preparation can be ensured by removing the material in that plaque with a pasteur pipette (a "plaque pick") and using this material as the inoculum for further growth cycles of the phage. The bacteriophage produced in such cycles represent a single strain or "monophage." The purity of phage preparation (including confirmation that it is a monophage and not a polyvalent phage preparation) is assessed by a combination of electron microscopy, SDS-PAGE, DNA restriction digest and analytical ultracentrifugation. In addition, each phage is uniquely identified by its DNA restriction digest profile, protein composition, and/or genome sequence.

Individual VRE-active bacteriophage strains (i.e., monophages) are propagated as described for enrichment culture above, and then tested for activity against multiple VRE strains to select broad-spectrum VRE-active bacteriophage. Efforts are made to select phages that (i) are lytic, (ii) are specific to enterococci, (iii) lyse more than 70% of the VRE strains in our VRE strain collection, and/or (iv) lyse VRE strains resistant to other VRE phages previously identified. It is also possible to select appropriate phages based upon the sequences of DNA or RNA encoding proteins involved in the binding and/or entry of phage into their specific host, or based upon the amino acid sequences or antigenic properties of such proteins.

Quantities of broad-spectrum VRE-active bacteriophage needed for therapeutic uses described below may be produced by culture on a suitable host strain in the mariner described above for enrichment culture. When performing an enrichment culture to produce bacteriophage for therapeutic use, a host strain is selected based on its ability to give a maximum yield of phage, as determined in pilot experiments with several different host VRE strains. If two or more host strains give similar yield' the strain most sensitive to antibiotics is selected.

The techniques described herein for isolation of VRE monophages are applicable to isolation of bacteriophages that are lytic for other pathogenic bacteria. Substitution of host strains of other bacteria will result in isolation of phage specific for those bacteria. Starting the isolation process with samples that also contain bacteria of the host species will accelerate the process.

Isolation of phage for MDRSA or for resistant Pseudomonas species can be accomplished by a skilled artisan in a fashion completely analogous to the isolation of VRE phage.

Patient Population

Any patient who is at risk for colonization with VRE, MDRSA, multi-drug resistant Pseudomonas, or other antibiotic-resistant species, or who has proven VRE colonization is a candidate for treatment according to the method of this invention. Intestinal colonization with VRE is relatively common in institutionalized patients undergoing antimicrobial therapy. In studies conducted in 1993–94, 17–19% of a random sample of all patients at the University of Maryland Hospital were colonized with VRE (Morris, et al. (1995), "Enterococci resistant to multiple antimicrobial agents including vancomycin." *Ann. Int. Med.*, 123:250–9), while in an identical study conducted in 1996 this increased to 23.8%. Once colonized with VRE, a patient may remain colonized for life; however once off antimicrobial therapy, VRE colonization may drop to levels not detectable in routine stool culture. Colonized persons though who also subsequently become immunocompromised are at risk for developing bacteremia (Edmond, et al., 1995; Tornieporth, et al (1996), "Risk factors associated with vancomycin resistant Enterococcus faecium colonization or infection in 145 matched case patients and control patients." *Clin. Infect Dis.*, 23:767–72).

VRE infection is a particularly serious problem among immunocompromised and/or seriously ill patients in cancer centers, intensive care units, and organ transplant centers. In case control studies VRE has been linked to antimicrobial use and severity of illness (as measured by APACHE score) (Handwerger, et al. (1993), "Nosocomial outbreak due to Enterococcus faecium, highly resistant to vancomycin, penicillin and gentamicin." *Clin. Infect Dis.*, 16:750–5; Montecalvo, et al. (1996), "Bloodstream infections with vancomycin resistant enterococci." *Arch. Intern. Med.*, 156:1458–62; Papanicolaou, et al. (1996), "Nosocomial infections with vancomycin-resistant Enterococcus faecium in liver transplant patients: Risk factors for acquisition and mortality." *Clan. Infect. Dis.*, 23:760–6; Roghmann, et al., (1997), "Recurrent vancomycin resistant Enterococcus faecium bacteremia in a leukemic patient who was persistently colonized with vancomycin resistant enterococci for two years." *Clin. Infect Dis.*, 24;514–5). Investigators at the University of Maryland at Baltimore and the Baltimore VA Medical Center have demonstrated by pulse field electrophoresis that VRE strains causing bacteremia in cancer patients are almost always identical to those that colonize the patient's gastrointestinal tract.

Three categories of immunocompromised patients subjected to prolonged antimicrobial administration in a institutionalized setting and who would be susceptible to VRE gastrointestinal colonization are: 1) leukemia (30,200 patients per year in the U.S.) and lymphoma patients (64,000 patients per year in the U.S.), 2) transplant patients (20,961 per year in the U.S.), and 3) AIDS patients (66,659 patients per year in the U.S.). The total number of patients in the immunocompromised category is 181,800 per year in the U.S. Pfundstein, et al., found that the typical rate of enterococcal gastrointestinal colonization among renal and pancreas transplant patients receiving antibiotics in an institutional setting was 34% (38/102) with 4 (11%) of these isolates being VRE (Pfundstein, et al. (1999), "A randomized trial of surgical antimicrobial prophylaxis with and without vancomycin in organ transplant patients." *Clin. Transplant.*, 13:245–52). Therefore the rate of gastrointestinal colonization by VRE in this immunocompromised population would be 0.34×0.11=0.04 or 4% of the total patient population. One can therefore estimate VRE gastrointestinal, colonization to be 181,800×0.04=7272 patients per year.

Formulation and Therapy

According to this invention, VRE-active bacteriophage are preferably formulated in pharmaceutical compositions containing the bacteriophage and a pharmaceutically acceptable carrier, and can be stored as a concentrated aqueous solution or lyophilized powder preparation. Bacteriophage may be formulated for oral administration by resuspending purified phage preparation in aqueous medium, such as deionized water, mineral water, 5% sucrose solution, glycerol, dextran, polyethylene glycol, sorbitol, or such other formulations that maintain phage viability, and are non-toxic to humans. The pharmaceutical composition may contain other components so long as the other components do not reduce the effectiveness (ineffectivity) of the bacteriophage so much that the therapy is negated. Pharmaceutically acceptable carriers are well known, and one skilled in the pharmaceutical art can easily select carriers suitable for particular routes of administration (Remington's Pharmaceutical Sciences, Mack Publishing Co., Easton, Pa., 1985).

The pharmaceutical compositions containing VRE-active bacteriophage may be administered by parenteral (subcutaneously, intramuscularly, intravenously, intraperitoneally, intrapleurally, intravesicularly or intrathecally), topical, oral, rectal, inhalation, ocular, otic, or nasal route, as necessitated by choice of drug and disease.

Injection of specific lytic phages directly into the bloodstream can eliminate or significantly reduce the number of targeted bacteria in the blood. If, after either oral or local administration, phages get into the bloodstream in sufficient numbers to eliminate bacteria from the bloodstream, septicemia may be treated by administering phages orally (or locally). If the phages do not get into the bloodstream in sufficient numbers to eliminate bacteria from the bloodstream, the utility of direct i.v. injection of phages for treating septic infections can be used to treat bloodstream infections caused by VRE and other pathogenic bacteria, and can provide an urgently needed means for dealing with currently untreatable septicemic infections.

Dose and duration of therapy will depend on a variety of factors, including the patient age, patient weight, and tolerance of the page. Bacteriophage may be administered to patients in need of the therapy provided by this invention by oral administration. Based on previous human experience in Europe, a dose of phage between $10^7$ and $10^{11}$ PFU will be suitable in most instances. The phage may be administered orally in, for example, mineral water, optionally with 2.0 grams of sodium bicarbonate added to reduce stomach acidity. Alternatively, sodium bicarbonate may be administered separately to the patient just prior to dosing with the phage. Phages also may be incorporated in a tablet or capsule which will enable transfer of phages through the stomach with no reduction of phage viability due to gastric acidity, and release of fully active phages in the small intestine. The frequency of dosing will vary depending on how well the phage is tolerated by the patient and how effective a single versus multiple dose is at reducing VRE gastrointestinal colonization.

The dose of VRE-active bacteriophage and duration of therapy for a particular patient can be determined by the skilled clinician using standard pharmacological approaches in view of the above factors. The response to treatment may be monitored by, analysis of blood or body fluid levels of VRE, or VRE levels in relevant tissues or monitoring disease state in the patient. The skilled clinician will adjust the dose and duration of therapy based ors the response to treatment revealed by these measurements.

One of the major concerns about the use of phages in clinical settings is the possible development of bacterial resistance against them. However, as with antimicrobial resistance, the development of resistance to phages takes time. The successful use of phages in clinical settings will require continual monitoring for the development of resistance, and, when resistance appears, the substitution of other phages to which the bacterial mutants are not resistant. In general, phage preparations may be constructed by mixing several separately grown and well-characterized lytic monophages, in order to (i) achieve the desired, broad target activity of the phage preparation, (ii) ensure that the preparation has stable lytic properties, and (iii) minimize the development of resistance against the preparation.

The development of neutralizing antibodies against a specific phage also is possible, especially after parenteral administration (it is less of a concern when phages are administered orally and/or locally). However, the development of neutralizing antibodies may not pose a significant obstacle in the proposed clinical settings, because the kinetics of phage action is much faster than is the host production of neutralizing antibodies. For VRE for example, phages will be used for just a few days, sufficient to reduce VRE colonization during the time period when immunocompromised patients are most susceptible to the development of potentially fatal VRE septicemia, but not long enough for phage-neutralizing antibodies to develop. If the development of antiphage antibodies is a problem, several strategies can be used to address this issue. For example, different phages having the same spectrum of activity (but a different antigenic profile) may be administered at different times during the course of therapy. On a more sophisticated level, therapeutic phages may be genetically engineered which will have a broad lytic range and/or be less immunogenic in humans and animals.

Environmental Therapy

In the 1980's a number of British studies were conducted which demonstrated the efficacy of bacteriophage prophylaxis and therapy in mice and farm animal models. These studies were significant because the titers of the phage preparations administered were significantly less than the bacterial inoculum indicating in vivo bacteriophage multiplication. For example, Smith et al (Smith, et al. (1982), "Successful treatment of experimental *Escherichia coli* infections in mice using phage: its general superiority over antibiotics." *J. Gen. Microbiol.*, 128:307–1825) found intramuscular inoculation of mice with $10^6$ CFU of *E. coli* with K1 capsule killed 10/10 mice. However when mice were simultaneously intramuscularly inoculated with $10^4$ PFU of phage, at a separate site, 10/10 mice survived. Smith and coworkers demonstrated that administration of a mixture of two phage resulted in high levels of protection of calves with diarrhea induced by *E. coli* with K 88 or K99 fimbriae (Smith, et alg. (1983), "Effectiveness of phages in treating experimental *Escherichia coli* diarrhea in calves, piglets and lambs." *J. Gen. Microbiol.*, 129:2659–75; Smith, et al. (1987), "The control of experimental *Escherichia coli* diarrhea in calves by means of bacteriophage." *J. Gen. Microbiol.*, 133:1111–26; Smith, et al. (1987), "Factors influencing the survival and multiplication of bacteriophages in calves and in their environment." *J. Gen. Microbiol.*, 133:1127–35). If the phage was administered before or at tire same time as *E. coli* no deaths occurred and complete protection was attained. Control animals developed watery diarrhea and died within 2 to 5 days. If phage administration was delayed until the onset of diarrhea, protection was not complete although the severity of infection was greatly reduced and no deaths were observed. Berchieri, et al., found that fewer chicks orally infected with $10^9$ PFU of *Salmonella typhimurium* died when $10^9$ PFU of Salmonella specific phage was orally administered soon after initiation of the bacterial infection (Berchieri, et al. (1991), "The activity in the chicken alimentary tract of bacteriophages lytic for *Salmonella typhimurium.*" *Res. Microbiol.*, 142:541–49). They also found that the phage was readily spread between the different infected birds.

Environmental applications of phage in health care institutions could lie most useful for equipment such as endoscopes and environments such as ICUs which maybe potential sources of nosocomial infection due to pathogens such as VRE but which may be difficult or impossible to disinfect. Phage would be particularly useful in treating equipment or environments inhabited by bacterial genera such as Pseudomonas which may become resistant to commonly used disinfectants. In the Soviet Union there has been a report that application of phage to the hospital environment has resulted in killing targeted bacteria such as Staphylococci and Pseudomonas within 48–72 hours. Phage persisted in the environment as long as there were target bacteria present and upon elimination of target bacteria, phage became undetectable in 6–8 days (Alavidze, et al, 1988, "Use of specific bacteriophage in the prophylaxis of intrahospital infections caused by *P. aeruginosa*." in Abstracts., All-Soviet Union conference "Modern biology at the service of public health". Kiev, Ukraine).

Phage compositions used to disinfect inanimate objects or the environment may be sprayed, painted, or poured, onto such objects or surfaces in aqueous solutions with phage titers ranging between $10^7$–$10^{11}$ PFU/ml. Alternatively, phage may be applied by aerosolizing agents that might include dry dispersants which would facilitate distribution of the phage into the environment. Such agents may also be included in the spray if compatible with phage viability and nontoxic in nature. Finally, objects may be immersed in a solution containing phage. The optimal numbers and timing of applications of phage compositions remains to be determined and would be predicated by the exact usage of such products.

Since phage are normally widely present in the environment and are found even in food or drugs, there is minimal safety concern with regard to applying phage preparations to the environment.

As reported above, Smith and Huggins in England found that *E. coli* induced diarrhea in calves could be prevented by simply spraying the litter in the calf rooms with an aqueous phage preparation or even by keeping the calves in uncleaned rooms previously occupied by calves whose *E. coli* infections had been treated with phage. There is also data from the Soviet Union indicating the efficacy of phage to rid chicken houses of Staphylococci (Ponomarchuk, et al., (1987), "Strain phage Staphylococci applicable for prophylaxis and therapy of poultry Staphylococcus." Soviet patent N1389287, Dec. 15, 1987).

In the future, application of VRE phage to the environment of farm animals such as chickens or cattle maybe necessary to reduce VRE in this setting if VRE become prevalent in such environments and such animal VRE are capable, upon being consumed ire contaminated food, of transiently colonizing the human gastrointestinal tract long enough to transfer antibiotic resistance gene transposons to normal gut flora (Latta, S. (1999) "Debate heats up over antibiotic-resistant foodborne bacteria." *The Scientist* 13; (14) 4–5).

Bacteriophage Cocktails

This invention also contemplates phage cocktails which may be custom tailored to the pathogens that are prevalent in a certain situation. Typically, pathogenic bacteria would be initially isolated from a particular source (e.g., a patient or location contaminated with VRE) and susceptibility testing of the pathogens to various bacteriophage strains would be performed, analogous to antimicrobial susceptibility testing. Once each pathogen's phage susceptibility profile is determined, the appropriate phage cocktail can be formulated from phage strains to which the pathogens are susceptible and administered to the patient. Since phage would often be used in institutional settings where pathogens are resistant to many antimicrobial agents, phage cocktails would often consist of phage lytic for the most prevalent institutional pathogens which, in addition to enterococci, are *Staphylococcus aureus, Staphylococcus epidermidis, E. coli* and *Pseudomonas aeruginosa*. Also since enterococci are often involved in polymicrobial infections along with other gastrointestinal commensals, such as in pelvic wound infections, the approach of therapeutically using cocktails of phage lytic against different bacterial species would be most appropriate. Since phage cocktails would be constructed of phage against institutional pathogens, isolation of such phage would be most successful from the sewage of such institutions. Typically, the phage cocktail will include one or more VRE-active bacteriophage according to this invention.

It may be appropriate to use certain phage cocktails in agricultural settings where there are certain human pathogens such as Salmonella and Campylobacter inherent to poultry or livestock and which contaminate the environment of such animals on an ongoing basis. The result is a continuing source of infection by such pathogens.

Bacteriophage cocktails may be applied contemporaneously—that is, they may be applied at the same time (e.g., in the same application), or may be applied in separate applications spaced in time such that they are effective at the same time. The bacteriophage may be applied as a single application, periodic applications, or as a continuous application.

Other bacteria within the contemplation of the present invention include, inter alia, Campylobacter, *E. coli* H7:0157, and Listeria, and Stapholocoocus.

Bacteriophages as Sanitation Agents

Phages may be used as sanitation agents in a variety of fields. Although the terms "phage" or "bacteriophage" may be used below, it should be noted that, where appropriate, this term should be broadly construed to include a single bacteriophage, multiple bacteriophages, such as a bacteriophage cocktail, and mixtures of a bacteriophage with an agent, such as a disinfectant, a detergent, a surfactant, water, etc.

The efficacy of phage treatment to reduce bacterial load may be determined by quantitating bacteria periodically in samples taken from the treated environment. In one embodiment, this may be performed daily. If administration of phage reduced bacterial load by at least 1 log as compared to the control (e.g., before treatment) within 48–98 hours after phage administration, then this dose of the particular phage is deemed efficacious. More preferably, colonization will be reduced by at least 3 logs.

Applications

According to some embodiments of the present invention, bacteriophages may be used for food and agriculture sanitation (including meats, fruits and vegetable sanitation), hospital sanitation, home sanitation, military sanitation (including anti-bioterrorism applications and military vehicle and equipment sanitation), industrial sanitation, etc. Other applications not specifically mentioned are within the contemplation of the present invention.

1. Food and Agriculture Sanitation

The broad concept of bacteriophage sanitation may be applied to other agricultural applications and organisms. Produce, including fruits and vegetables, dairy products, and other agricultural products consumed by humans may become contaminated with many pathogenic organisms, including Salmonella and highly virulent organisms such as

*E. coli* O157:H7. For example, freshly-cut produce frequently arrive at the processing plant contaminated with pathogenic bacteria at concentrations ranging from $10^4$ to $10^6$ colony forming units (CFU) per gram of food. *Salmonella enteritidis* is able to survive and grow on fresh-cut produce under conditions mimicking "real life" settings, and fresh-cut fruits having a less acidic pH (e.g., a pH of about 5.8; such as honeydew melons) are especially prone to becoming overgrown with Salmonella.

A significant proportion of produce consumed in the United States originates in countries lacking the high sanitation standards of the United States. In the past, this has led to outbreaks of food-borne illness traceable to imported produce. The application of bacteriophage preparations to agricultural produce can substantially reduce or eliminate the possibility of food-borne illness through application of a single phage or phage cocktails with specificity toward species of bacteria associated with food-borne illness. Bacteriophage may be applied at various stages of production and processing to reduce bacterial contamination at that point or to protect against contamination at subsequent points.

During the studies performed by the inventors in collaboration with Intralytix, Inc., it has been shown that the SCLPX phage mixture reduces the numbers of Salmonella on honeydew melon slices by approximately 3.5 log units (see Example 7). This level of reduction is significantly higher than the maximum reduction rate of 1.3 logs in bacterial counts reported for fresh-cut fruits using the most effective chemical sanitizer (hydrogen peroxide). See Liao, C. H. and G. M. Sapers "Attachment and growth of Salmonella Chester on apple fruits and in vivo response of attached bacteria to sanitizer treatments" *J. Food Prot.* 63:876–83 (2000); Beuchat, Nail, et al. 1998 1003. However, because some phages may have difficulty in withstanding acidic pH, the treatment may not be as effective on produce with an acidic pH, such as Red Delicious apples. With high pH produce, in one embodiment, higher concentrations of phages may be applied to the produce. In another embodiment, the administration of the phages to the produce may be repeated. In still another embodiment, pH-resistant phage mutants may be selected and applied to the highly acidic produce.

The use of specific phages as biocontrol agents on produce provides many advantages. Examples include the facts that phages are natural, non-toxic products that will not disturb the ecological balance of the natural microflora in the way the common chemical sanitizers do, but will specifically lyse the targeted food-borne pathogens. In this context, the SCLPX mixture is only effective against Salmonellae, and generally does not lyse other bacteria, such as *E. coli, S. aureus, P. aeruginosa*, Lactobacillus, Streptococcus, and enterococci. Should additional coverage be required, phages lytic for more than one pathogen can be combined and used to target several pathogenic bacteria simultaneously.

Phages also provide additional flexibility for long-term applications. For example, it has been reported that many bacteria are developing resistance to sanitizers commonly used in the fresh-cut produce industry. See Chesney, J. A., J. W. Eaton, and J. R. JR. Mahoney, "Bacterial Glutathione: a Sacrificial Defense against Chlorine Compounds" *Journal of Bacteriology* 178:2131–35 (1996); Mokgatla, R. M., V. S. Brözel, and P. A. Gouws "Isolation of Salmonella Resistant To Hypochlorous Acid From A Poultry Abattoir" *Letters in Applied Microbiology* 27:379–382 (1998). Although it is likely that resistance will also eventually develop against certain phages, there are important differences between phages and chemical sanitizers that favor the use of phages as biocontrol agents. For example, the development of resistance against phages can be reduced by constructing and using a cocktail of phages containing several lytic phages (similar to the SCLPX preparation), so that when the bacteria develop resistance to one phage in the preparation, the resistant mutants will be lysed by other phages and will not be able to propagate and spread further. Furthermore, because phages, unlike chemical sanitizers, are natural products that evolve along with their host bacteria, new phages that are active against recently emerged, resistant bacteria can be rapidly identified when required, whereas identification of a new effective sanitizer is a much longer process which may take several years.

In one embodiment, the use of specific bacteriophages, in addition to washing of fresh-cut produce with water and keeping the produce at low temperatures (approximately 50° C.), provides an efficient method for preventing food-borne human pathogens, like Salmonella, from growing and becoming a health hazard on at least some produce, including freshly-cut, damaged, diseased, and healthy produce.

Specific bacteriophages may be applied to produce in restaurants, grocery stores, produce distribution centers, etc. For example, phage may be periodically or continuously applied to the fruit and vegetable contents of a salad bar. This may be though a misting or spraying process, washing process, etc., and may be provided as a substitute or supplement to chemical sanitizers, such as hypochlorite, sulfur dioxide, etc.

In another embodiment, phage may be periodically or continuously applied to produce in a grocery store. In still another embodiment, phage may be applied to produce in produce distribution centers, in shipment vehicles, etc. Other applications are within the contemplation of the present invention.

A bacteriocin may also be applied to the produce. In one embodiment, bacteriocin nisin, which is sold under the name Nisaplin®, and available from Aplin & Barrett Ltd, Clarks Mill, Stallard Street, Trowbridge, Wilts BA14 8HH, UK, may be used. Nisin is produced by Lactococcus strains, and has been used to control bacterial spoilage in both heat-processed and low-pH foods. Nisin is active against Listeria monocytogenes, especially at low pH, which complements the phage application.

Another embodiment of this application contemplates inclusion of bacteriophage or matrices or support media containing bacteriophages with packaging containing meat, produce, cut fruits and vegetables, and other foodstuffs. Bacteriophage preparations containing single bacteriophages or cocktails of bacteriophages specific for the desired pathogen(s) may be sprayed, coated, etc. onto the foodstuff or packaging material prior to packaging. The bacteriophage preparation may also be introduced into the package as part of a matrix that may release adsorbed or otherwise incorporated phage at a desirable rate by passive means, or may comprise part of a biodegradable matrix designed to release phage at a desirable rate as it degrades. Examples of passive release devices may include absorbent pads made of paper or other fibrous material, sponge, or plastic materials.

In another embodiment, a polymer that is suitable for packaging may be impregnated with a bacteriophage preparation. A suitable method for impregnating a polymer with a bacteriophage preparation is disclosed in U.S. Patent No. 60/175,377, which is incorporated by reference in its entirety. Suitable polymers may include those polymers approved by the U.S. Food and Drug Administration for food packaging.

In another embodiment, bacteriophage preparations specific for *Clostridium botulinum* may be a desirable means of preventing botulism in foodstuffs such as bacon, ham, smoked meats, smoked fish, and sausages. Present technology requires high concentrations of nitrates and nitrites in order to meet the United States Government standard for *C. botulinum*. Bacteriophage preparations would permit reduction or possible elimination of these potentially carcinogenic substances. Methods of application include spraying as an aerosol, application of liquid to the surface with a spreading device, injection of a liquid, or incorporation of a liquid bacteriophage preparation into products requiring mixing.

2. Hospital Sanitation

Bacteriophages may be used to sanitize hospital facilities, including operating rooms, patient rooms, waiting rooms, lab rooms, or other miscellaneous hospital equipment. This equipment may include electrocardiographs, respirators, cardiovascular assist devices, intraaortic balloon pumps, infusion devices, other patient care devices, televisions, monitors, remote controls, telephones, beds, etc. The present invention provides a fast and easy way to sanitize certain sensitive equipment and devices.

In some situations, it may be desirable to apply the phage through an aerosol canister; in other situations, it may be desirable to wipe the phage on the object with a transfer vehicle; in still other situations, it may be desirable to immerse the object in a container containing phages; and in others, a combination of methods, devices, or techniques may be used. Any other suitable technique or method may be used to apply the phage to the area, object, or equipment.

Phages may be used in conjunction with patient care devices. In one embodiment, phage may be used in conjunction with a conventional ventilator or respiratory therapy device to clean the internal and external surfaces between patients. Examples of ventilators include devices to support ventilation during surgery, devices to support ventilation of incapacitated patients, and similar equipment. This may include automatic or motorized devices, or manual bag-type devices such as are commonly found in emergency rooms and ambulances. Respiratory therapy devices may include inhalers to introduce medications such as bronchodilators as commonly used with chronic obstructive pulmonary disease or asthma, or devices to maintain airway patency such as continuous positive airway pressure devices.

In another embodiment, phage may be used to cleanse surfaces and treat colonized people in an area where highly-contagious bacterial diseases, such as meningitis or enteric infections such as those caused by Shigella species have been identified. Bacterial meningitis, such as meningitis caused by *Neisseria meningitides* frequently occurs in settings where children or young adults are closely clustered such as schools, dormitories, and military barracks. The pathogen is spread as an aerosol. Shigella is commonly spread through fecal-oral transmission, where the spread may be direct, or may be through intermediary contaminated surfaces or food or water. Bacterial pathogens spread as an aerosol may be treated through introduction of bacteriophage into the environment as an aerosol continuously or episodically. Bacterial infections spread through contact with contaminated surfaces may be treated with appliances to distribute bacteriophage-containing preparations into those surfaces. Contaminated water, most specifically contaminated water supplies such as cisterns, wells, reservoirs, holding tanks, aqueducts, conduits, and similar water distribution devices may be treated by introduction of bacteriophage preparations capable of lysing the intended pathogen.

3. Home and Public Area Sanitation

In another embodiment, bacteriophages may be used to sanitize a living area, such as a house, apartment, condominium, dormitory, barracks, etc. The phage may also be used to sanitize public areas, such as theaters, concert halls, museums, train stations, airports, etc.

The phage may be dispensed from conventional devices, including pump sprayers, aerosol containers, squirt bottles, pre-moistened towelettes, etc. The phage may be applied directly to (e.g., sprayed onto) the area to be sanitized, or it may be transferred to the area via a transfer vehicle, such as a towel, sponge, etc.

Phage may be applied to various rooms of a house, including the kitchen, bedrooms, bathrooms, garage, basement, etc. In embodiment, the phage may be used in the same manner as conventional cleaners (e.g., Lysol® cleaner, 409® cleaner, etc.).

In one embodiment, phage may be applied in conjunction with (before, after, or simultaneously with) conventional cleaners provided that the conventional cleaner is formulated so as to preserve adequate bacteriophage biologic activity.

In one embodiment, phage may be used to sanitize pet areas, such as pet beds, litter boxes, etc.

4. Military Applications

Bacteriophages may be used to decontaminate military equipment. In one embodiment, this may include decontaminating vehicles, aircraft, weapons, miscellaneous soldier equipment, etc. that have been contaminated by biological weapons or agents, such as Anthrax. Aircraft and other equipment with sensitive outer surfaces, such as stealth aircraft, or sensitive electronics located on or near those surfaces, may be damaged, or destroyed, by the application of known decontamination fluids or techniques. Thus, this damage may be avoided by using bacteriophages to decontaminate these surfaces.

In one embodiment, the phage may be sprayed on the equipment by hoses or other spraying devices. In another embodiment, a "car wash" may be constructed to coat a vehicle with phages as the vehicle passes through the "car wash." Other methods, apparatuses, techniques, and devices are within the contemplation of this invention.

Bacteriophages may also be used to combat bioterrorism and biologic warfare, which is defined as the intentional introduction of pathogenic bacteria into the environment by means where it is likely to infect human populations and cause disease. Bioterrorism may include introduction of pathogenic bacteria into buildings, vehicles, food supplies, water supplies, or other similar settings. Biologic warfare may involve dispersal of pathogenic bacteria by missiles, explosive devices, aircraft, ships, and other similar devices in ways likely to infect targeted populations or individuals.

In one embodiment, bacteriophage may be used to decontaminate large objects, including the interior and exterior of buildings. Here, the phage may be sprayed or otherwise applied to contaminated surfaces. In another embodiment, the phage may be used to decontaminate large areas of land. For example, the phage may be applied by crop sprayers (e.g., both fixed-wing and rotary wing aircraft), by irrigation sprinklers, or by any suitable means.

Where appropriate, the application of a bacteriophage cocktail is within the contemplation of the present invention.

5. Industrial Applications

The present invention may be used in many industrial applications, including the animal husbandry industry. This includes, but is not limited to, the breeding, raising, storing, and slaughter of livestock or other animals.

Referring to FIG. 1, an example of how to use bacteriophage in a poultry processing plant is provided. It should be recognized that phages may be applied at any stage; the preferred locations for the phage application are identified in this figure. Although the word "spray" may be used in conjunction with the description below, it should be recognized that rinsing (e.g., in a washing tank) and providing phages as a food or a drinking additive (e.g., mixing the phages with food or water, or both), where appropriate, may be substituted, or used in conjunction with spraying.

After the fertilized eggs are collected in the Fertilized Egg Collection Site, the fertilized eggs may be sprayed with phages before they are transferred to incubators in the hatchery (A). It has not been possible to consistently eliminate Salmonella from breeder flocks, and, consequently, Salmonella may be present on the surface of fertilized eggs; conditions in incubators promote multiplication of the organism, and chicks may become infected as they peck out of the egg. Aggressive washing of eggs and the use of disinfectants of sufficient strength to eliminate all bacterial contamination is not desirable with fertilized eggs. In this setting, spraying phages onto the surface of the eggs may provide a means of minimizing Salmonella contamination of hatched chicks.

After the birds are hatched, the birds may be sprayed with phages before they are transferred to a chicken house or to a farm (B). Immediately after hatching, chicks may be sprayed with various viral vaccines (Newcastle, bronchitis, INDIA) which are ingested as the animals preen their feathers. A small percentage of chicks are Salmonella-positive at this point in time (see comments above about Salmonella on eggs); however, once introduced into chicken houses, contamination may spread rapidly to all animals in the house. Application of phage immediately after hatching and before transfer to chicken houses may reduce the risk of the bacterium being spread from the chicks to the rest of the birds in the chicken house.

During raising in the chicken house or farm, the birds may be provided with phages in their drinking water, food, or both (C). Once mature, the birds are transferred to the slaughter area, where they are slaughtered, and then transferred to a washing area, where they are processed and washed. Phages may be sprayed onto the chicken carcasses after the chlorine wash in chiller tanks, before post-chill processing (D). Salmonella contamination at this point should be minimized, and application of phages may provide a "final product clean-up." In addition, only a small amount of phage preparation will be needed (approximately 5–10 ml per chicken) instead of several hundred liters required to decontaminate a chicken house. Another advantage of applying phages at this stage is that since phages will not be carried to loci where they can readily be exposed to Salmonella for a long period of time (e.g., to a chicken house), the risk of Salmonella developing resistance against the phage(s) will be greatly reduced.

After slaughter, the birds are chilled. The chilled birds are then processed, which may include sorting, cutting the birds, packaging, etc., and are then transported to designated points of sale.

It is also possible to sanitize the areas that the birds contact. This includes the egg collection site, the incubator/hatchery, the chicken house, the slaughter area, and the processing areas, and any equipment that is used or contained therein. Similar procedures may be employed for the reduction of bacterial contamination on eggs produced for sale and/or consumption. In addition to use contemplated for Salmonella, this method may be particularly well suited to the decontamination of environmental pathogens, specifically including *Listeria monocytogenes*.

In one embodiment, the working phage concentration may range from $1\times10^5$–$1\times10^9$ PFU/ml.

One of ordinary skill in the art should recognize that the example provided in FIG. 1 is easily adaptable for other species of animals, including calves, pigs, lamb, etc, even if the animals are not slaughtered. For example, the present invention may have applications in zoos, including cages, holding areas, etc.

Where appropriate, the application of a bacteriophage cocktail is within the contemplation of the present invention.

In another embodiment, phages may be applied to industrial holding tanks. For instance, in areas in which products are milled, water, oil, cooling fluids, and other liquids may accumulate in collection pools. Specific phages may be periodically introduced to the collection pools in order to reduce bacterial growth. This may be through spraying the phage on the surface of the collection pool, wherein it is most likely that the bacteria may be located, or through adding phage into the collection pool.

Devices

1. General

According to one embodiment of the present invention, phages may stored in a container, and then applied to an area or an object. The container may range in size from a small bottle to a large industrial storage tank, which may be mobile or fixed.

The container of the present invention may use a variety of mechanisms to apply the phage to an object. In general, any mechanism that provides a substantially even dispersion of the phage may be used. Further, the phage should be dispersed at a pressure that does not cause substantial damage to the object to which the phage is being applied, or at a pressure that causes damage, directly or indirectly, to the phage itself.

It has been found that some bacteriophages may be inactivated due to interfacial forces, while other bacteriophages survive such forces. Adams suggested that air-water interface was responsible for bacteriophage inactivation. See Adams, M. H. "Surface inactivation of bacterial viruses and of proteins" *J. Gen. Physiol.* 31:417–432 (1948) (incorporated by reference in its entirety). In addition, Adams found that it is the presence of proteins in the diluent protected the several *coli*-dysentery bacteriophages from inactivation.

Trouwborst et al. conducted several studies on bacteriophage inactivation. See Trouwborst, T., J. C. de Jong, and K. C. Winkler, ."Mechanism of inactivation in aerosols of bacteriophage $T_1$" *J. Gen. Virol.* 15:235–242 (1972); Trouwborst, T., and K. C. Winkler "Protection against aerosol-inactivation of bacteriophage $T_1$ by peptides and amino acids" *J. Gen. Virol.* 17:1–11 (1972); Trouwborst, T., and J. C. de Jong "Interaction of some factors in the mechanism of inactivation of bacteriophage MS2 in aerosols" *Appl. Microbiol.* 26:252–257 (1973); and Trouwborst, T., S. Kuyper, J. C. de Jong, and A. D. Plantinga "Inactivation of some bacterial and animal viruses by exposure to liquid-air interfaces" *J. Gen. Virol.* 24:155–165 (1974), all of which are incorporated, by reference, in their entireties. In "Mechanism of inactivation in aerosols of bacteriophage $T_1$," the data suggested that survival of the bacteriophage $T_1$ varied with relative humidity, with a minimum survival near the relative humidity corresponding to a saturated solution of the salt, and a better survival at a lower initial salt concentration. The authors found when the $T_1$ bacteriophage was shaken, or when it was an aerosol, surface inactivation was a major cause of inactivation. The data suggested, however, that broth protected $T_1$ against aerosol inactivation. Subsequently, in "Protection against aerosol-inactivation of bacteriophage $T_1$ by peptides and amino acids," Trouwborst et al. determined that the phage $T_1$ may be protected from aerosol-inactivation by peptone and by apolar amino acids, such as leucine and phenylalanine. In addition, the authors found that peptone also protects $T_1$ from inactivation from low relative humidity.

In "Inactivation of some bacterial and animal viruses by exposure to liquid-air interfaces," Trouwborst et al. subjected the bacteriophages $T_1$, $T_3$, $T_5$, $MS_2$, of the EMC virus and of the Semliki Forest virus to a large air/water interface. The authors determined that the EMC virus was not sensitive to this treatment, phage $T_3$ and $T_5$ were little affected, and phage $T_1$ and the Semliki Forest virus were rapidly inactivated. The authors also found that inactivation by aeration could be prevented by the addition of peptone, by apolar carboxylic acids, and by the surface active agent OED. Further, the data suggested that the rate of surface inactivation was strongly dependent on the salt concentration of the medium.

In a study conducted by Thompson and Yates ("Bacteriophage Inactivation at the Air-Water-Solid Interface in Dynamic Batch Systems" *Applied and Environmental Microbiology*, 65:1186–1190 (March 1999), which is incorporated by reference in its entirety), three bacteriophages (MS2, R17 and $\Phi$X174) were percolated through tubes containing glass and Teflon beads. Two of the three phages (MS2 and R17) were inactivated by this action, while the third bacteriophage ($\Phi$X174) was not. The data suggested to the authors that inactivation was dependent upon (1) the presence of a dynamic air-water-solid interface (where the solid is a hydrophobic surface), (2) the ionic strength of the solution, (3) the concentration of surface active compounds in the solution, and (4) the type of virus used.

In addition, in a separate study, Thompson et al. studied the air-water interface and its inactivating effect on certain bacteriophages. See Thompson et al., "Role of the Air-Water-Solid Interface in Bacteriophage Sorption Experiments", *Applied and Environmental Microbiology*, 64:304–309 (January 1998) (which is incorporated by reference in its entirety). In this study, it was observed that the bacteriophage MS2 was inactivated in control tubes made of polypropylene, while there was no substantial inactivation of MS2 in glass tubes. In contrast, the bacteriophage $\Phi$X174 did not undergo inactivation in either polypropylene or glass tubes. This data suggested that the inactivation of MS2 was due to the influence of air-water interfacial forces, while $\Phi$X174 was not affected by the same forces that inactivated MS2.

At least one study has been directed at the type, characteristics, and properties of membrane. See Mix, T. W. "The physical chemistry of membrane-virus interactions" *Dev. Ind. Microbiol.* 15:136–142 (1974) (incorporated by reference in its entirety). Mix identified several factors to be considered when determining whether a virus will adsorb onto a membrane, including the nature of the membrane and the virus surfaces, electrostatic forces, environmental factors (pH, the presence of electrolytes, the presence of competitive adsorbents, temperature, flow rate, etc.). The importance of the factors may vary for different viruses.

The devices discussed below may be appropriate for most bacteriophages; however, it may be possible to enhance delivery of specific bacteriophages by selecting for phages that are stable in specific devices before they are used for the indicated purposes. In addition, it may be beneficial to use different materials (e.g., glass versus polypropylene) depending on the particular bacteriophage. For example, the studies above suggest that the phage $\Phi$X174 would be effective if dispensed from through a polypropylene tube and a sprayer, such that a plurality of drops of the phage were formed, while the studies suggest that the phage MS2 would not be effective in this application regime. Therefore, appropriate devices, materials, and phages should be selected.

In some embodiments, the phage may be maintained under controlled conditions in order to maintain the activity level of the phage, such as in an aqueous or a non-aqueous solution, a gel, etc. In another embodiment, the phage may be stored in a freeze-dried state, and may be mixed with a liquid vehicle shortly before use. Suitable vehicles include water, chloroform, and mixtures thereof. Other vehicles include water containing biologically compatible solutes such as salts and buffering agents as are commonly known in the art. Such salts and buffering agents may also consist of volatile solutes, such as ammonium chloride, or may be non-volatile, such as sodium chloride. This embodiment is expressly intended to include all combinations and mixtures of aqueous and organic solvents and solutes that maintain adequate phage viability, which may be greater than 50% of the original titer, more preferably greater than 75% of the original titer, or most preferably greater than 95% of the original titer.

In another embodiment, the phage may be maintained at a controlled temperature. In another embodiment, the phage may be maintained at a controlled pressure.

2. Specific Devices

In one embodiment, a simple manual spray mechanism may be used. In this device, the pressure is generated by the user when the user depresses the pump (or, if a trigger pump, when the user pulls the "trigger"), causing the phage and its carrier to be forced through the nozzle of the mechanism. In another embodiment, the phage may be stored under pressure in an canister, and may be delivered in a conventional manner by depressing a button, or a valve, on top of the canister. In another embodiment, a fogger or misting device may be used to disperse the phage over an area.

In addition to manual sprayers, power sprayers may be used to apply the phage. Example of a suitable sprayer includes the Power Painter, the AmSpray® Double Spray Piston Pump, the High Volume Low Pressure pumps, and the Diaphragm pumps, available from Wagner Spraytech Corporation, Minneapolis, Minn. Other power sprayers, including those much larger than those listed above, are within the contemplation of the present invention.

In another embodiment, rollers, such as a paint roller, may be used. This may include thin film applicators. Within the contemplation of the present invention are roller devices, including a roller device connected to a supply of phage that is forced through the roller onto a surface.

Power rollers may also be used. For example, the Wagner® Power Roller available from Wagner Spraytech Corporation, Minneapolis, Minn. may be used. Other power rollers are also within the contemplation of the present invention.

For larger applications, hoses, sprayers, sprinklers, or other suitable devices may be used to apply the phage to the area or to the object from the container.

The phage may also be applied manually. For example, the phage may be applied to the object with a brush. In another embodiment, a transfer vehicle, such as a cloth wipe, a paper wipe, a towel, a towelette, a sponge, etc. may be used to apply the phage to the object. The transfer vehicle may be wiped across an area, or an object, to apply the phage to the area or object. In one embodiment, the transfer vehicle may be prepackaged, similar to an alcohol wipe.

As discussed above, the phage may be stored in its freeze-dried form, and then combined with the solvent shortly before use. In on embodiment, a package with a glass ampoule containing a solvent may include a material coated with the phage in freeze-dried form. When a user wishes to use the phage, the user crushes the ampoule, causing the solvent to mix with the phage. Other technologies for storing the phage and solvent separately, and causing their mixture shortly before use, are well-known, and may also be used.

In another embodiment, a device that maintains the activity of the phage may be used. For example, a device that is similar to a fire extinguisher or hand-held plant sprayer may be used to store at least one bacteriophage under a temperature and pressure that is sufficient to maintain the activity of the phage(s). This may include providing a temperature control device in order to maintain the temperature, which may be powered by A/C current, batteries, etc.

The device may be portable, such that it may be taken to decontamination sites, or stored in decontamination chambers, etc.

In one embodiment, the phage may have a predetermined "shelf-life," and may be periodically changed. In one embodiment, the device may include a sensor that warns when the activity level of the phage reaches a predetermined level.

In another embodiment, multiple compartments may be provided for multiple phages, which may be mixed before dispersal from the device. Compartments for at least one agent, such as water, foams, disinfectants, and other agents may be provided, and may also be mixed with the phage(s) before dispersal, or may be dispersed separately.

The phage may also be maintained in gels and foams. Thus, devices that dispense gels or foams may be used.

EXAMPLES

Example 1

Obtaining VRE Isolates

Isolation of VRE

VRE were isolated by standard methods from patients in the surgical intensive care and intermediate care units of the University of Maryland Medical Center in Baltimore. Trypticase Soy Agar supplemented with 5% sheep blood (BBL, Cockeysville Md.) was used to isolate enterococci from urine, wounds and sterile body fluids. VRE were isolated from stool specimens on Colistin Nalidixic Acid (CNA) agar (Difco labs, Detroit, Mich.) supplemented with defibrinated sheep blood (5%), vancomycin (10 $\mu$g/ml) and amphotericin (1 $\mu$g/ml). See Facklam, R. R., and D. F. Sahm. 1995. Enterococcus. In: Manual of Clinical Microbiology, 6$^{th}$ edition, American Society for Microbiology, Washington, D.C., pp. 308–312.

Identification of VRE

Enterococci were identified by esculin hydrolysis and growth in 6.5% NaCl at 45° C. Identification to the species level was done using conventional testing as indicated in Facklam and Collins (Facklam, et al. (1989), "Identification of Enterococcus species isolated from human infections by a conventional method test scheme." J. Clin. Microbiol., 27:731–4).

Antimicrobial Susceptibility Testing of VRE

Antimicrobial susceptibilities to ampicillin, vancomycin, streptomycin, and gentamicin were determined using the E test quantitative minimum inhibitory concentration procedure (AB Biodisk, Solna Sweden). Quality control stains of E. faecium (ATCC 29212, 51299) were used to ensure potency of each antimicrobial agent tested. With exception of vancomycin, susceptibility interpretations from the National Committee for Clinical Laboratory Standards were adhered to (National Committee for Clinical Laboratory Procedures (1993), "Methods for Dilution Antimicrobial Susceptibility Tests for Bacteria that Grow Aerobically." 3rd Edition. National Committee for Clinical Laboratory Standards Villanova Pa.; National Committee for Clinical Laboratory Standards (1993), "Performance Standards for Antimicrobial Disk Susceptibility Tests" 5th Edition, National Committee for Clinical Laboratory Standards, Villanova Pa.). A VRE isolate was defined as one that had a minimum inhibitory concentration to vancomycin of at least 16 $\mu$g/ml.

Defining Generically Distinct VRE Strains

Distinct VRE isolates were characterized as such by contour-clamped homogeneous electric field electrophoresis after digestion of chromosomal DNA with SmaI (Verma, P. et al. (1994) "Epidemiologic characterization of vancomycin resistant enterococci recovered from a University Hospital" (Abstract). In; Abstracts of the 94th General Meeting of the American Society for Microbiology, Las Vegas Nev.; Dean, et al. (1994) "Vancomycin resistant enterococci (VRE) of the vanB genotype demonstrating glycoprotein (G) resistance inducible by vancomycin (V) or teicoplanin (T)" In; Abstracts of the 94th General Meeting of the American Society for Microbiology, Las Vegas Nev.). Electrophoretic studies were also performed using ApaI digestion for VRE strains which differed only by 1–3 bands after initial analysis (Donabedian, S. M. et al (1992) "Molecular typing of ampicillin-resistant, non-beta lactamase producing Enterococcus faecium isolates from diverse geographic areas." J. Clin. Microbiol., 30; 2757–61). The vancomycin-resistant genotype (vanA, vanB or vanC) was defined by polymerase chain reaction analysis using specific primers selected from published gene sequences (Goering, R. V. and the Molecular Epidemiological Study Group (1994) "Guidelines for evaluating pulsed field restriction fragment patterns in the epidemiological analysis of nosocomial infections." (Abstract) Third International Meeting of Bacterial Epidemiological Markers; Cambridge England).

Example 2

Isolation of VRE Phage 500 ml of raw sewage from the University of Maryland is mixed with 100 ml of 10 times concentrated LB broth (Difco Laboratories). This sewage-broth mixture is inoculated with a 18–24 hour LB broth culture (1 ml) of a VRE strain and incubated at 37° C. for 24 hours to enrich the mixture for bacteriophage which can infect the VRE strain added. After incubation, the mixture is centrifuged at 5000 g for 15 minutes to eliminate matter which may interfere with subsequent filtration. The supernatant is filtered through a 0.45 $\mu$m Millipore filter. Filtrate is assayed using the Streak Plate Method and/or Appelman Tube Turbidity Test to detect lytic activity against different strains of VRE.

Method for testing phage against VRE isolates

Three methods are employed: Plaque Assay; Streak Plate Method; and Tube Turbidity Method, and the procedures for each follow.

Plaque Assay:

A 18–24 hour nutrient broth culture of the VILE strain (0.1 ml) to be tested for susceptibility to infection and dilutions of a VRE phage preparation (1.0 ml) are mixed and then added to 4.5 ml 0.7% a molten agar in nutrient broth at 45° C. This mixture is completely poured into a petri dish containing 25 ml of nutrient broth solidified with 2% agar. During overnight incubation at 37° C., VRE grow in the agar and form a confluent lawn with some VRE cells being infected with phage. These phages replicate and lyse the initially infected cells and subsequently infect and lyse neighboring bacteria. However the agar limits the physical spread of the phage throughout the plate, resulting in small visibly clear areas called plaques on the plate where bacteriophage has destroyed VRE within the confluent lawn of VRE growth.

The number of plaques formed from a given volume of a given dilution of bacteriophage preparation is a reflection of the titer of the bacteriophage preparation. Also since one plaque with a distinct morphology represents one phage particle that replicated in VRE in that area of the bacterial lawn, the purity of a bacteriophage preparation can be ensured by removing the material in that plaque with a pasteur pipette (a "plaque pick") and using this material as the inoculum for further growth cycles of the phage. On this basis, doing further plaque assays on preparations of phage grown from this plaque pick, one would expect all plaques to have a single appearance or plaque morphology which is the same as the plaque picked, a further indication of purity. Therefore this technique can not only be used to test bacteriophage potency but also bacteriophage purity.

Streak Plate Method:

Eighteen hour LB broth cultures of the different enterococci strains to be tested are grown at 37° C. (resulting in approximately $10^9$ CPU/ml) and a loopful of each culture is streaked across a nutrient agar plate in a single line. This results in each plate having a number of different VRE streaked across it in single straight lines of growth. Single drops of phage filtrates to be tested are applied to the steaks of each VRE growth, and the plate is incubated 6 hours at 37° C., at which time the steaks of the different VRE strains are examined for the ability of phage to form clear areas devoid of bacterial growth, indicating lysis of that particular VRE strain by that particular phage.

The VRE host range for a given phage filtrate can be ascertained by which VRE streaks it is capable of causing a clear area devoid of growth and which strains of VRE the phage is incapable of doing this.

Appelman Tube Turbidity Test (from Adams, M. H. 1959. Bacteriophages. Interscience Publ. New York N.Y.):

18 hour LB broth cultures of different VRE strains are prepared. 0.1 ml of phage filtrate or a dilution thereof is added to 4.5 ml of VRE broth cultures and incubated at 37° C. for 4 hours (monophages), or 4–18 hours (polyvalent phages). Phage free VRE broth cultures are used as controls. Broth cultures which are normally turbid due to bacterial growth are examined for the ability of the phage to lyse the VRE strain as indicated by the clearing of the culture turbidity.

The host range of a given phage can be ascertained by which VRE broth cultures the phage is capable of clearing and which broth cultures it cannot induce clearing.

Example 3

A Phage Strain Is Active Against Over 200 VRE Isolates

A collection of 234 VRE isolates; 187 *E. faecium* of which 3 strains are from ATCC, 41 *E. faecalis* strains, and 6 *E. gallinarium* strains as well as 6 *E. faecium* strains which are vancomycin sensitive were tested for susceptibility of infection by 7 monophages isolated as described in Example 2. Susceptibility of infection was determined by the 3 techniques described. The majority of VRE strains in this collection were isolated from patients at the University of Maryland and Baltimore VA Medical Centers as indicated in Example 1. Such VRE isolates were determined to be distinct and genetically diverse by pulsed field gel electrophoresis typing. Of the 7 monophages, VRE/E2 and VRE/E3 have a relatively narrow host range compared to other VRE phages, but are able to infect the small proportion of VRE strains which were resistant to other phages collected. A phage cocktail containing the above 7 VRE monophages lysed 95% of the VRE strains in the collection.

Example 4

Producing Bacteriophage-containing Compositions 0.1 ml amounts of a 18–24 LB broth culture (LB broth culture contains Bacto LB Broth. Miller (Luria-Bertani, dehydragted) reconstituted according to instructions by Difco Laboratories, Detroit, Mich.) of a strain of VRE, which has been previously selected on the basis of being able to produce a maximum yield of bacteriophage are mixed with 1.0 ml of a VRE monophage filtrate and then mixed with 4.5 ml of 0.7% molten agar in nutrient broth at 45° C. This mixture is completely poured into a petri dish containing 25 ml of nutrient broth solidified with 2% agar. After overnight incubation at 37° C., the soft top agar layer with the phage is recovered by gently scraping it off the plate, and this recovered layer is mixed with a small volume of broth (1 ml per plate harvested), This suspension is centrifuged at 5,000–6,000 g for 20 minutes at 4° C. and the phage containing supernatant is carefully removed. The supernatant is filtered through a 0.45 μm filter and centrifuged at 30,000 g for 2–3 hours at 4° C.

The phage containing pellet is suspended in 1–5 ml of phosphate buffer and is further purified by ion exchange chromatography using a Q resource ion exchange column (Pharmacia Biotech, Piscataway, N.J.) and a 0–1 M NaCl gradient in the start buffer. Phage tends to be eluted from the column between 150–170 mM NaCl with each fraction being assessed for the presence of phage by standard plaque assay technique. Fractions collected and assayed are pooled if the phage titer by the plaque assay is no greater than 3 logs lower than the phage preparation put onto the column (e.g., $10^{10}$ PFU/ml is put onto the column therefore pool only those fractions with titers >$10^7$ PFU/ml). Pooled fractions are tested for endotoxin by the Limulus Amebocyte Lysate Assay (BioWhittaker Inc., Walkersville, Md.). Pools demonstrating >50 EU/ml of endotoxin are passed through a Affi-prep polymyxin support column (Bio-Rad Labs, Hercules, Calif.) to remove residual endotoxin.

The phage pool is buffer exchanged against 100 mM ammonium bicarbonate using size exclusion with Sephadex G-25 chromatography (Pharmacia Biotech). 1 ml aliquots of the purified phage are freeze dried in the presence of gelatin and stored at room temperature. The purity of the phage preparation is assessed by a combination of electron microscopy, SDS-PAGE, DNA restriction digest and analytical ultracentrifugation.

Example 5

Determination of a Protective Dose of Bacteriophage

Establishment of sustained VRE colonization in a animal model.

CD-1 mice are pretreated for seven days with 0.1 mg/ml of gentamicin and 0.5 mg/ml of streptomycin in drinking water to reduce their normal intestinal flora. VRE are then administered to the mice, who have fasted for 6 hours, by consumption of one food pellet inoculated with $10^6$ CFU of VRE. VRE intestinal colonization is confirmed in mice by standard colony counts of $>10^3$ CFU VRE/gram of feces on CNA agar containing 10 µg/ml of vancomycin, 1 µg/ml of amphotericin B and 10 µg/ml of gentamicin. The colonization procedure is considered successful if there is consistent shedding of $>10^3$ CFU of VRE per gram of feces for 5–7 days after consumption of the spiked food pellet. VRE colonization may persist for 4 weeks by this method. Mice are given drinking water containing the above mixture of antibiotics throughout the duration of the experiment.

Use of a to vivo mouse model to demonstrate efficacy of lytic bacteriophage in reducing VRE gastrointestinal colonization.

Twenty-four hours after detecting $>10^3$ CFU VRE/gram of feces, mice were administered VRE phage (by having there consume one food pellet inoculated with $10^9$ PFU of VRE). Control groups consisted of (1) non-VRE-colonized mice sham dosed (no phage in dose), (2) VRE-colonized mice which are sham dosed, and (3) non-VRE-colonized mice dosed with phage. Five mice were used in each group.

The efficacy of phage treatment to reduce VRE gastrointestinal colonization was determined by quantitating VRE, on a daily basis, in weighed fecal samples from the mice in the different groups. In addition, at the end of the experiment, mice were sacrificed and the number of VRE and phage in their liver, spleen, and blood determined. If administration of phage reduced VRE gastrointestinal colonization/overall load in mice by at least 1 log as compared to the control groups within 48–98 hours after phage administration, then this dose of the particular phage was deemed efficacious. More preferably, colonization was reduced by at least 3 logs.

Example 6

Isolation and Characterization of Lytic Phages Against Selected Salmonella Serotypes Isolation and purification of bacteriophages.

Salmonella-specific bacteriophages were isolated, by standard techniques, from various environmental sources in Maryland. Purification was performed by a combination of low- and high-speed centrifugation and by sequential fractionation with various chromatographic media. Purified phages were buffer-exchanged against physiological phosphate-buffered saline, pH 7.6. The final product was sterilized using a 0.22 micron filter, titered, and stored in sterile glass ampules at 40 C.

Bacteriophage isolates were tested against a strain collection which consisted of 245 Salmonella strains, including *S. hadar* (84 strains), *S. typhimurium* (42 strains), *S. enteritidis* (24 strains), *S. heidelberg* (2×strains) and *S. newport* (18 strains). Forty-four of the remaining 56 strains were grouped in 17 serotypes and 12 strains were untypable. Genetically, this was a diverse strain population encompassing 78 PFGE types.

Seven clones of Salmonella-specific lytic bacteriophages were isolated from environmental sources. Electron microscopy identified them as "tailed phages" of the family Myoviridae and Siphoviridae. The most active phage clone lysed 220 (90%) of the strains, including all DT-104 (multi-drug resistant) Salmonella isolates. The second most active phage lysed 74% of the strains.

Pulsed field gel electrophoresis (PFGE).

The rapid PFGE procedure developed for typing *E. coli* 0157:H7 strains was used for PFGE typing of the Salmonella strains [5]. All strains were analyzed after digesting their DNA with Xba I, and selected strains were also analyzed after digesting their DNA with Avr II and Spe I restriction enzymes. The CDC-standard S. newport strain am01144 (Xba I-digested) was used as the reference strain in all experiments. Since the number of Salmonellae strains per PFGE type was limited, it was not determined whether there was an association between certain clonal groups and resistance/susceptibility to these phages.

The "target range" was further increased by 5% by constructing a "cocktail of phages" consisting of three phages. This "cocktail" was efficacious in reducing Salmonella counts on experimentally contaminated surfaces, and spraying $1\times10^5$ PFU of phage reduced the numbers of Salmonella from $1\times10^7$ CFU to undetectable levels in less than 48 h. The phage clones and the cocktail were not active against other bacterial species tested, including *E. coli, P. aeruginosa, S. aureus, K. pneumoniae* and *L. monocytogenes*, which suggests that their activity is confined to the Salmonella species.

Environmental decontamination studies.

The bottoms of approximately two autoclaved plastic boxes (A and B) comprising approximately 225 $cm^2$ each in surface area were evenly covered with a test Salmonella strain ($1\times10^7$ CFU). After 1 hour, box A was sprayed with approximately 3 ml of an aqueous suspension of a Salmonella phage ($1\times10^7$ PFU/ml), and box B was sprayed with 3 ml of sterile water. Swab samples were taken at 3, 6, 24 and 48 hours, and they were assayed, by standard techniques, to determine the numbers of Salmonella and phage.

In the environmental decontamination studies, 3 hours after phage treatment there was a significant reduction of approximately 2.5 logs in the number of Salmonella on box A, as compared to the "no phage" box B. Salmonella was not detectable on the phage-exposed box (box A) after 24–48 h, which corresponds to at least a 3 log drop in counts (compared to the group that was not treated with phages). We have conducted additional experiments examining the effect of phages on (i) various concentrations ($1\times10^5$ and $1\times10^3$ CFU) of Salmonella, and (ii) various concentrations ($1\times10^5$ and $1\times10^3$ CFU) of a mixed Salmonella contamination (3 strains of different serotypes). In all cases, phages reduced the Salmonella to undetectable levels in 24–48 h. Testing after prolonged exposure (10 days) indicated that there was no regrowth of Salmonella, and the phages were still detectable at low (approximately $1\times10^1$ PFU) levels. These data suggest that Salmonella-specific phage preparations may have utility in reducing/eliminating Salmonella contamination from environmental surfaces, and, therefore, may be useful in decontaminating poultry plants, chicken houses, etc.

Finished poultry product decontamination studies:

Chickens purchased at retail (2 chickens per group) were experimentally contaminated with a rifampin-resistant, phage-sensitive Salmonella strain ($1\times10^3$ CFU per bard), and they were kept at room temperature for 1 hour. A phage cocktail (10 ml, 1×10⁷ PFU/ml) was sprayed on the chickens in group 3A, and the chickens in group 2A were sprayed with sterile water. The chickens were analyzed for the presence of the test Salmonella strain using the USDA/FSIS standard methodology for Salmonella detection.

The results of the finished poultry product decontamination studies showed that the number of Salmonella recovered from the phage-treated group (group 3A) was approximately $10^3$-fold less than that recovered from the; phage-untreated, control group (group 2A). These data suggest that Salmonella-specific phages may have utility in final poultry product clean up; i.e., reduce/eliminate residual Salmonella contamination of post-chill birds.

Carefully constructed, potent, Salmonella-specific phage preparations containing one or more lytic monophages may have utility in reducing/eliminating Salmonella contamination from environmental surfaces, and, therefore, may be useful in decontaminating poultry plants, chicken houses, etc. Moreover, Salmonella-specific phages may be useful in final poultry product clean up; i.e., reduce/eliminate residual Salmonella contamination of post-chill birds.

Example 7

Bacteriophage Sanitation of Freshly-Cut Produce

A study was performed to determine (i) the survival and growth of Salmonella enteritidis (choleraesuis) on fresh-cut apple and honeydew melon slices under the conditions (temperature, humidity, and length of incubation) likely to be encountered during their processing and storage, and (ii) the effectiveness of specific phages for use as a biocontrol agent on fresh-cut fruits contaminated with Salmonella.

Fruit.

All of the fruits were disinfected with 70% EtOH before slicing. "Red Delicious" apples stored at 1° C. were cut into eight slices with an apple slicer and wounded (Conway, W. S., B. Leverentz, R. A. Saftner, W. J. Janisiewicz, C. E. Sams, and E. Leblanc "Survival and growth of Listeria monocytogenes on fresh-cut apple slices and its interaction with *Glomerella cingulata* and *Penicillium expansum*" *Plant Disease* 84:177–181 (2000)). Honeydew melons purchased from a local supermarket were sliced through the equator with a sterile knife. Two rings were cut out of the center of each melon, and each ring was cut into 12 equal slices. The pH ranges of the apples and honeydew melon tissues determined with a pH combination electrode, Semi-Micro (81–03 RosS™, Orion Research, Inc., Beverly, Mass.). were pH 4.1–4.7 and pH5.7–5.9, respectively.

Preparation of the bacterial inoculum.

A rifampicin-resistant, phage preparation-susceptible *Salmonella enteritidis* strain, from the bacterial strain collection of Intralytix, Inc. (Baltimore, Md.), was used to experimentally contaminate the apple and honeydew melon slices. The bacterium was grown overnight at 37° C. on L-Agar supplemented with 100 µg/ml rifampicin (Sigma #R-3501), the bacteria were collected and washed with sterile saline (0.9% NaCl), and the bacterial suspension was diluted to a concentration of 1×10⁶ CFU/ml.

Phage.

The phage mixture (SCPLX-phage) containing 4 distinct lytic phages specific for *Salmonella enteritidis* was obtained from Intralytix at a concentration of $10^{10}$ PFU/ml in phosphate-buffered saline. The mixture was diluted with sterile saline (10⁷ PFU/ml final concentration), immediately before applying onto the fruit slices.

Bacterial inoculation and phase application.

Twenty-five µl of the bacterial suspension were applied to wounds made in the fruit slices. After applying the Salmonella strain, 25 µl of the phage mixture were applied to the wounds, and the slices were placed in 475-ml Mason jars covered with plastic film. Real View laboratory sealing film (Norton Performance Plastics, location?) was used to seal jars containing the apple slices and a Std-Gauge film with a high oxygen transfer rate type LDX5406, product 9NK27 (Cryovac, Duncan, S.C.) was used to seal the jars containing the honeydew melon slices.

Recovery of bacteria and phages.

After inoculation, the Mason jars containing the fruit slices were stored at 5, 10 and 20° C. The number of CFU/ml on the apple and honeydew melon slices was determined at 0, 3, 24, 48, 120, and 168 h (4 fruit slices per treatment for each recovery time) after inoculation. Recovery and quantitation of the bacteria was performed according to the procedure described previously. After plating the samples, the remaining sample solution was filter-sterilized (0.45 µm Supor membrane, Acrodisk, Pall Gelman) and stored at 4° C. The titer of the phage in this filtrate was determined according to standard procedures (Adams, M. H. "Bacteriophages" *Interscience Publishers,* New York. (1959)).. All experiments were repeated at least twice to ensure reproducibility.

RAPD and PFGE.

The RAPD technique was performed, according to the manufacturer's instructions, using a RAPD kit (Amersham Pharmacia Biotech, Piscataway, N.J.) containing ready-to-go analysis beads, and the DNA patterns were analyzed by electrophoresis in 2% agarose gel in TAE buffer. PFGE was performed using the CHEF Mapper (Bio-Rad Laboratories, Hercules, Calif.), as described previously.

Statistical analyses.

The numbers of CFU/wound on apple slices were analyzed as a three-factor general linear model using PROC MIXED (SAS/STAT® Software: Changes and Enhancements through Release 6.12, pp. 1167. Cary, N.C. 1997 ("SAS Institute")) with treatment, temperature and time as the factors. The assumptions of the general linear model were tested. To correct variance heterogeneity, the values were $\log_{10}$ transformed, (log x) and treatments were grouped into similar variance groups for the analysis. The means were compared using pair-wise comparisons with Sidak adjusted p-values so that the experiment-wise error for the comparison category was 0.05.

The analysis for the honeydew data was done in two parts, since the values for 5° C. at 120 and 168 h were all zero.

Part 1:

The CFU values for 0, 3, 24, and 48 h were analyzed as a three-factor general linear model using PROC MIXED (SAS Institute) with treatment, temperature and time as the factors. The assumptions of the general linear model were tested. To correct variance heterogeneity, the values were $\log_{10}$ plus one transformed, (log (x+1)) and treatments were grouped into similar variance groups for the analysis. The means were compared using pair-wise comparisons with Sidak adjusted p-values so that the experiment-wise error for the comparison category was 0.05. To test for the influence of time or temperature on the phage treatment, the magnitude of the difference between the phage treatment and the control at each temperature at a given time was tested against the difference for the other temperatures at the same time.

Part 2:

The CFU values for 0, 3, 24, 48,120 and 168 at 10° C. and 20° C. were analyzed as a four-factor general linear mixed model using PROC MIXED (SAS Institute) with treatment, temperature and time as the fixed factors and experiment as the random factor. The assumptions of the general linear model were tested. To correct variance heterogeneity, the values were $\log_{10}$ plus one transformed, (log (x+1)) and treatments were grouped into similar variance groups for the analysis. The means were compared using pair-wise comparisons with Sidak adjusted p-values so that the experiment-wise error for the comparison category was 0.05. To test for the influence of time or temperature on the phage treatment, the magnitude of the difference between the phage treatment and the control at 10° C. was tested against the difference for 20° C. at each time period.

Results a. Salmonella growth on fruit.

*Salmonella enteritidis* survived at 5° C. and grew at 10 and 20° C. on "Red Delicious" apple slices (pH 4.1–4.7) and honeydew melon slices (pH 5.7–5.9) stored during a time of 168 h. As expected, the most vigorous bacterial growth was observed on the fresh-cut fruits stored at 20° C., with the number of bacteria rapidly increasing (by approximately 3.5 logs) on both honeydew melons and "Red Delicious" apples within the first 24 h after inoculation, and further increasing on honedew melons by additional 2 logs. In general, Salmonella grew better on honeydew melons than apples, with the most profound difference (approximately 2 logs) observed at 168 h between the groups incubated at 20° C. At a lower temperature (4° C.), cell populations were stagnant and the Salmonella did not grow noticeably on either of the fresh-cut fruits tested; on honeydew melons, the bacterial population actually decreased starting from 120 h of incubation.

Several steps were taken to ensure that no wild-type Salmonella strains (that initially may have been present on the fruit surface) were cultured. For example: (i) the fruits' uncut surfaces were cleaned with 70% ethanol at the beginning of each experiment, and (ii) rifampin (150 $\mu$g/ml) was included in the selective media, in order to ensure that only the original, rifampin-resistant test strain was quantitated. In addition, 10–15 randomly selected colonies were analyzed by RAPD and/or PFGE after each experiment, and the patterns were compared to that of the test *S. enteritidis* strain.

b. Phage persistence on fruit.

The mixture of *Salmonella enteritidis*-specific phages continually declined by about 3 log units on honeydew melon over a period of 168 h. This decline was similar for all temperatures. In contrast, the phage concentration on the apple slices decreased by approximately 6 log after 3 h, the phage could not be detected after 24 h at 10 and 20° C. and after 48 h at 5° C. In order to determine whether different acidity of "Red Delicious" apples (pH 4.2) and honeydew melons (pH 5.8) was responsible for this difference, we determined phage titers in the aliquots of the SCPLX preparation incubated (4° C.) at pH 4.2 and 5.8 for 48 h. Approximately 4 times more phages were recovered from the aliquots incubated at pH 5.8 than from those incubated at pH 4.2 (data not shown).

c. Pathogen control by the phage treatment.

The bacterial count was consistently lower (by approximately 3.5 logs) on the honeydew melon treated with the phage mixture than on corresponding samples of the control. There was no significant difference between the numbers of Salmonella on the apple slices in the control and test groups. In general, the effect of the phage mixture was independent of temperature and time during the duration of the experiment (see Table 1, below). The only significant effect attributed to temperature occurred at 48 h of incubation, when the phage mixture suppressed S. enteritidis populations on honeydew melon more at 10° C. than at 20° C. (see Table 2, below). Statistical analysis of the differences between the treatments at various times and temperatures did not reveal any other effect of these parameters on the phage treatment of honeydew melon (see Table 3, below). Phage susceptibility testing of the bacteria that survived phage treatment indicated that they did not develop resistance against phages in the SCPLX preparation.

TABLE 1

Log (CFU) Mean Comparisons for Honeydew

| treatment | honeydew part 1 | part 2 |
|---|---|---|
| control | 3.17a* | 4.97a* |
| phage treatment | 1.38b | 3.74b |

*Treatment means with different letters are different at significance level ≤0.0001.

TABLE 2

Comparisons of Treatment Differences between Temperatures at a Specific Time on Honeydew

| | p-value | | |
|---|---|---|---|
| time [h] | 5 vs. 10° C. | 5 vs. 20° C. | 10 vs. 20° C. |
| part 1 | | | |
| 0 | 0.2764 | 0.5645 | 0.5562 |
| 3 | 0.4685 | 0.8058 | 0.5473 |
| 24 | 0.1873 | 0.4964 | 0.2921 |
| 48 | 0.3450 | 0.0437 | 0.0039 |
| part 2 | | | |
| 120 | n/d | n/d | 0.9497 |
| 168 | n/d | n/d | 0.4119 |

TABLE 3

Analysis of Variance

| | p-values | | |
|---|---|---|---|
| source | 'Red Delicious' | honeydew part 1 | honeydew part 2 |
| treatment | 0.0060 | 0.0001 | 0.0001 |
| temperature | 0.0001 | 0.0001 | 0.0001 |
| trt × temp | 0.0001 | 0.3594 | 0.3594 |
| time | 0.0001 | 0.0001 | 0.0001 |
| trt × time | 0.0060 | 0.2388 | 0.2388 |
| temp × time | 0.0001 | 0.0001 | 0.0001 |
| trt × temp × time | 0.0818 | 0.2556 | 0.2556 |

Deposit Information

Six bacteriophages have been deposited under the Budapest Treaty. These deposits were made on Jan. 5, 2001 with the American Type Culture Collection (ATCC), 10801 University Boulevard, Manassas, Va. 20110. These bacteriophages are identified, as follows:

| Phage |
|---|
| SA-36 |
| SPT-1 |
| MSP-71 |
| LIST-3 |
| ENT-7 |
| ECO-9 |

For purposes of clarity of understanding, the foregoing invention has been described in some detail by way of illustration and example in conjunction with specific embodiments, although other aspects, advantages and modifications will be apparent to those skilled in the art to which the invention pertains. The foregoing description and examples are intended to illustrate, but not limit the scope of the invention. Modifications of the above-described modes for carrying out the invention that are apparent to persons of skill in medicine, bacteriology, infectious diseases, pharmacology, and/or related fields are intended to be within the scope of the invention, which is limited only by the appended claims.

All publications and patent applications mentioned in this specification are indicative of the level of skill of those skilled in the art to which this invention pertains. All publications and patent applications are herein incorporated by reference to the same extent as if each individual publication or patent application was specifically and individually indicated to be incorporated by reference.

We claim:

1. A method for packaging foodstuff, comprising:
   a) providing a foodstuff;
   b) providing a packaging material comprising at least one bacteriophage; and
   c) packaging the foodstuff with the packaging material.
2. The method of claim 1, wherein the packaging material is coated with the at least one bacteriophage.
3. The method of claim 2, wherein the packaging material is coated by spraying the packaging material with the at least one bacteriophage.
4. The method of claim 1, wherein the foodstuff is selected from the group consisting of: produce, cut fruits and cut vegetables.

* * * * *